United States Patent [19]

Schoen et al.

[11] Patent Number: 5,430,144
[45] Date of Patent: Jul. 4, 1995

[54] BENZO-FUSED LACTAMS PROMOTE RELEASE OF GROWTH HORMONE

[75] Inventors: William R. Schoen, Edison; Matthew J. Wyvratt, Jr., Mountainside; Paul J. Hodges, Brick, all of N.J.

[73] Assignee: Merck & Co., Inc., Rahway, N.J.

[21] Appl. No.: 97,146

[22] Filed: Jul. 26, 1993

[51] Int. Cl.⁶ .............. C07D 223/16; C07D 243/12; C07D 281/10; A61K 31/55
[52] U.S. Cl. ..................... 540/461; 540/517; 540/521; 540/523
[58] Field of Search ............. 540/461, 517, 521, 523

[56] References Cited

U.S. PATENT DOCUMENTS

| | | | |
|---|---|---|---|
| 4,411,890 | 10/1983 | Momany | 424/177 |
| 5,206,235 | 4/1993 | Fisher et al. | 514/213 |
| 5,283,241 | 2/1994 | Bochis et al. | 514/183 |

Primary Examiner—Robert T. Bond
Attorney, Agent, or Firm—J. Eric Thies; David Rose

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused lactams as the active ingredient thereof are also disclosed.

6 Claims, No Drawings

BENZO-FUSED LACTAMS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

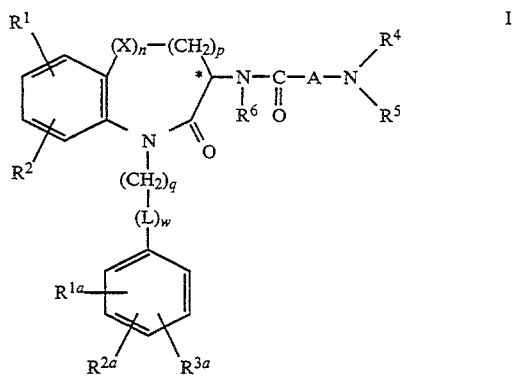

where
L is

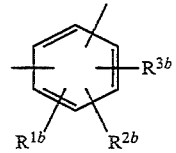

n is 0 or 1;
p is 0 to 3;
q is 0 to 4;
w is 0 or 1;
X is C=O, O, S(O)$_m$,

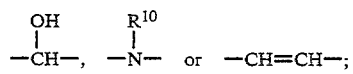

m is 0 to 2;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^{5b}$R$^{12b}$N(CH$_2$)$_v$—, R$^{7b}$CON(R$^{12b}$)(CH$_2$)$_v$—, R$^{5b}$R$^{12b}$NCO(CH$_2$)$_v$—, phenyl or substituted phenyl where the substituents are from 1 to 3 of halogen, $C_1$-$C_6$ alkyl, $C_1$-$C_6$ alkoxy, or hydroxy; and v is 0 to 3;
R$^{7a}$ and R$^{7b}$ are independently hydrogen, $C_1$-$C_3$ perfluoroalkyl, $C_1$-$C_6$ alkyl, substituted $C_1$-$C_6$ alkyl where the substitutents are phenyl or substituted phenyl; phenyl or substituted phenyl where the phenyl substitutents are from 1 to 3 of halogen, $C_1$-$C_6$ alkyl, $C_1$-$C_6$ alkoxy or hydroxy;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is

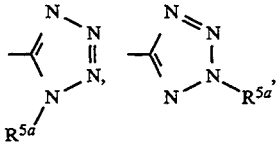

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^{5b}R^{12b}N(CH_2)_v$—, $R^{5b}R^{12b}NCO(CH_2)_v$—, $R^{5b}R^{12b}NCS(CH_2)_v$—, $R^{5b}R^{12c}NN(R^{12b})CO(CH_2)_v$—, $R^{5b}R^{12a}NN(R^{12b})CS(CH_2)_v$—, $R^{5b}R^{12b}NCON(R^{12a})(CH_2)_v$—, $R^{5b}R^{12b}NCSN(R^{12a})(CH_2)_v$—, $R^{5b}R^{12c}NN(R^{12b})CSN(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 3.

$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—(CH$_2$)$_s$— where B is $CHR^1$, O, $S(O)_m$ or $NR^{10}$, m is 0, 1 or 2, r and s are independently 0 to 3 and $R^1$ and $R^{10}$ are as defined.

$R^{13}$ is $C_1$-$C_3$ perfluoroalkyl, $C_1$-$C_6$ alkyl, substituted $C_1$-$C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy.

$R^{10}$ and $R^{11}$ are independently hydrogen, $C_1$-$C_6$ alkyl, phenyl, phenyl $C_1$-$C_6$ alkyl, $C_1$-$C_5$ alkoxycarbonyl or $C_1$-$C_5$ alkanoyl-$C_1$-$C_6$ alkyl;

$R^5$, $R^{5a}$ and $R^{5b}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl or substituted $C_3$-$C_{10}$ alkynyl where the substitutents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_{20}$ alkanoyloxy, $C_1$-$C_5$ alkoxycarbonyl, carboxy, formyl or —$NR^{10}R^{11}$ where $R^1$, $R^2$, $R^{10}$ and $R^{11}$ are as defined above;

$R^4$ is $R^{14}$ or $C_1$-$C_{10}$ alkyl substituted with $R^{14}$;

$R^{14}$ is

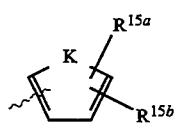

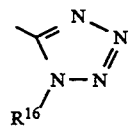

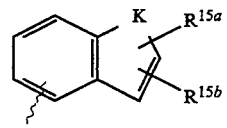

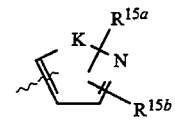

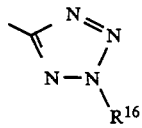

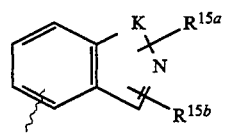

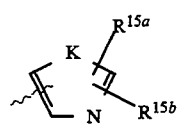

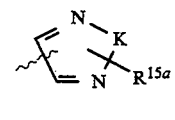

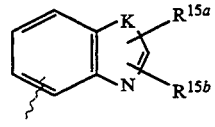

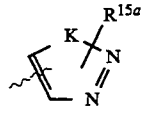

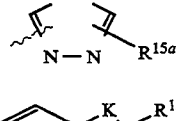

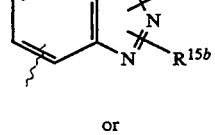

or

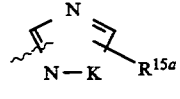

where
K is O, S or $NR^{16}$;
$R^{15a}$ and $R^{15b}$ are independently hydrogen, hydroxy, halogen, oxo, cyano, nitro, —$S(O)_mR^{7a}$, $C_1$-$C_3$ perfluoroalkyl, $C_1$-$C_3$ perfluoroalkoxy, $R^{12a}R^{12c}N(CH_2)_v$—, $R^{12a}R^{12b}NCO(CH_2)_v$—, $C_1$-$C_6$ alkoxy, phenyl, substituted phenyl, $C_1$-$C_{10}$ alkyl or substituted $C_1$-$C_{10}$ alkyl where the substituents on the phenyl or alkyl are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_6$ alkanoyloxy, $C_1$-$C_5$ alkoxycarbonyl, carboxy, formyl or —$NR^{10}R^{11}$ where $R^1$, $R^2$, $R^{7a}$, $R^{10}$, $R^{11}$, $R^{12a}$, $R^{12b}$, $R^{12c}$, m and v are as defined above;

$R^{16}$ is hydrogen, $C_1$-$C_6$ alkyl or substituted $C_1$-$C_6$ alkyl where the substitutents are from 1 to 3 of hydroxy, $C_1$-$C_6$ alkoxy, fluoro, $R^1$, $R^2$ independently disubstituted phenyl, $R^1$, $R^2$ independently disubstituted phenyl $C_1$-$C_3$ alkoxy, $C_1$-$C_6$ alkanoyloxy, $C_1$-$C_5$ alkoxycarbonyl, carboxy, $C_1$-$C_5$ alkanoyl-$C_1$-$C_6$ alkyl or —$NR^{10}R^{11}$ where $R^1$, $R^2$, $R^{10}$ and $R^{11}$ are as defined above;

$R^6$ is hydrogen, $C_1$-$C_{10}$ alkyl, phenyl or phenyl $C_1$-$C_{10}$ alkyl;

A is

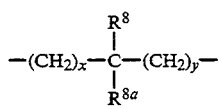

where
x and y are independently 0-3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, —$S(O)_mR^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^8$ and $R^{8a}$ can be taken together to form —$(CH_2)_t$— where t is 2 to 6; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are is methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Certain of the above defined terms may occur more than once in the above formula and upon such occurrence each term shall be defined independently of the other.

It is intended that the bond to $R^{14}$ can be to any of the available carbon or heteroatoms of the heteroaromatic group, including either ring of the benzo-fused heterocyclic groups, when the bonding is represented by a serpentine line.

Preferred compounds of the instant invention are realized when in the above structural formula:
n is 0 or 1;
p is 0 to 3;
q is 0 to 2;
w is 0 or 1;

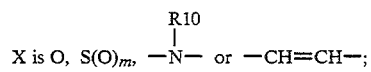

m is 0 to 2;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl where the substituents are phenyl; phenyl and v is 0 to 3;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is

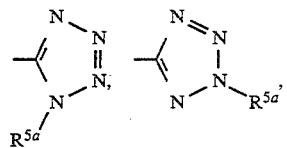

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12b}NCS(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12b}NCSN(R^{12a})(CH_2)_v$—, $R^{5b}R^{12c}NN(R^{12b})CSN(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 3.

$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined.

$R^{13}$ is $C_1$-$C_3$ perfluoroalkyl, $C_1$-$C_6$ alkyl, substituted $C_1$-$C_6$ alkyl, where the substitutents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy.

$R^{10}$ and $R^{11}$ are independently hydrogen, $C_1$-$C_6$ alkyl, phenyl $C_1$-$C_6$ alkyl, or $C_1$-$C_5$ alkanoyl-$C_1$-$C_6$ alkyl;

$R^5$, $R^{5a}$ and $R^{5b}$ are independently hydrogen, phenyl, substituted phenyl, $C_1$-$C_{10}$ alkyl or substituted $C_1$-$C_{10}$ alkyl where the substitutents on the phenyl or alkyl are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_{20}$ alkanoyloxy, $C_1$-$C_5$ alkoxycarbonyl, carboxy or formyl where $R^1$ and $R^2$ are as defined above;

$R^4$ is $R^{14}$ or $C_1$-$C_6$ alkyl substituted with $R^{14}$;

$R^{14}$ is as defined above;

$R^{15a}$ and $R^{15b}$ are independently hydrogen, hydroxy, halogen, —$S(O)_m R^{7a}$, $C_1$-$C_3$ perfluoroalkyl, $R^{12a}R^{12c}N(CH_2)_v$—, $R^{12a}R^{12b}NCO(CH_2)_v$—, $C_1$-$C_6$ alkoxy, phenyl, substituted phenyl, $C_1$-$C_{10}$ alkyl or substituted $C_1$-$C_{10}$ alkyl where the substitutents on the phenyl or alkyl are from 1 to 5 of hydroxy, $C_1$-$C_6$ alkoxy, fluoro, $R^1$, $R^2$ independently disubstituted phenyl, $R^1$, $R^2$ independently disubstituted phenyl $C_1$-$C_3$ alkoxy, $C_1$-$C_6$ alkanoyloxy, $C_1$-$C_5$ alkoxycarbonyl, carboxy or formyl where $R^1$, $R^2$, $R^{7a}$, $R^{12a}$, $R^{12b}$, $R^{12c}$, m and v are as defined above;

$R^{16}$ is hydrogen, $C_1$-$C_6$ alkyl or substituted $C_1$-$C_6$ alkyl where the substitutents are from 1 to 3 of hydroxy, $C_1$-$C_6$ alkoxy, fluoro, $R^1$, $R^2$ independently disubstituted phenyl, $R^1$, $R^2$ independently disubstituted phenyl $C_1$-$C_3$ alkoxy, $C_1$-$C_5$ alkoxycarbonyl, carboxy or $C_1$-$C_5$ alkanoyl-$C_1$-$C_6$ alkyl where $R^1$ and $R^2$ are as defined above;

$R^6$ is hydrogen, $C_1$-$C_{10}$ alkyl or phenyl $C_1$-$C_{10}$ alkyl;

A is

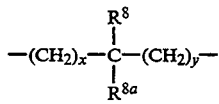

where x and y are independently 0-2;

$R^8$ and $R^{8a}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —$S(O)_m R^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^8$ and $R^{8a}$ can be taken together to form —$(CH_2)_t$— where t is 2 to 4; and $R^8$ and $R^{8a}$ can independently be joined to $R^5$ to form alkylene bridges between the terminal nitrogen and the alkyl portion of the A group wherein the bridge contains from one to five carbon atoms;

and pharmaceutically acceptable salts thereof.

Additional preferred compounds are realized in the above structural formula when:

n is 0 or 1;

p is 0 to 2;

q is 0 to 2;

w is 0 or 1;

X is $S(O)_m$ or —CH=CH—;

m is 0 to 1;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl or substituted $C_1$-$C_6$ alkyl where the substitutents are phenyl and v is 0 to 2;

$R^{3a}$ and $R^{3b}$ are independently hydrogen, $R^9$, $C_1$-$C_6$ alkyl substituted with $R^9$ or phenoxy substituted with $R^9$;

$R^9$ is

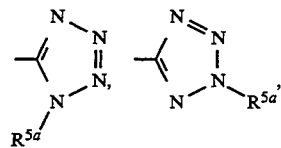

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12c}NN(R^{12b})CSN(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 2.

$R^{12a}$, $R^{12b}$ and $R^{12c}$ are independently $R^{5a}$ or $OR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined.

$R^{13}$ is $C_1$-$C_6$ alkyl, substituted $C_1$-$C_6$ alkyl, where the substitutents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy.

$R^{10}$ and $R^{11}$ are independently hydrogen, $C_1$-$C_6$ alkyl, phenyl $C_1$-$C_6$ alkyl, or $C_1$-$C_5$ alkanoyl-$C_1$-$C_6$ alkyl;

$R^5$, $R^{5a}$ and $R^{5b}$ are independently hydrogen, $C_1$-$C_{10}$ alkyl or substituted $C_1$-$C_{10}$ alkyl where the substitutents are from 1 to 5 of hydroxy, $C_1$-$C_6$ alkoxy, fluoro, $R^1$, $R^2$ independently disubstituted phenyl, $C_1$-$C_{20}$ alkanoyloxy, $C_1$-$C_5$ alkoxycarbonyl or carboxy where $R^1$ and $R^2$ are as defined above;

$R^4$ is $R^{14}$ or $C_1$-$C_3$ alkyl substituted with $R^{14}$;

$R^{14}$ is as defined above;

$R^{15a}$ and $R^{15b}$ are independently hydrogen, hydroxy, halogen, —$S(O)_m R^{7a}$, $R^{12a}R^{12c}N(CH_2)_v$—, $R^{12a}R^{12b}NCO(CH_2)_v$—, $C_1$-$C_6$ alkoxy, phenyl, substituted phenyl, $C_1$-$C_{10}$ alkyl or substituted $C_1$-$C_{10}$ alkyl where the substitutents on the phenyl or alkyl are from 1 to 5 of hydroxy, $C_1$-$C_6$ alkoxy, $R^1$, $R^2$ independently disubstituted phenyl, $C_1$-$C_6$ alkanoyloxy, $C_1$-$C_5$ alkoxycarbonyl, carboxy or formyl where $R^1$, $R^2$, $R^{7a}$, $R^{12a}$, $R^{12b}$, $R^{12c}$, m and v are as defined above;

$R^{16}$ is hydrogen, $C_1$-$C_6$ alkyl or substituted $C_1$-$C_6$ alkyl where the substitutents are from 1 to 3 of hydroxy, $C_1$-$C_6$ alkoxy, $R^1$, $R^2$ independently disubstituted phenyl, $C_1$-$C_5$ alkoxycarbonyl, carboxy or $C_1$-$C_5$ alkanoyl-$C_1$-$C_6$ alkyl where $R^1$ and $R^2$ are as defined above;

$R^6$ is hydrogen or $C_1$-$C_{10}$ alkyl;

A is

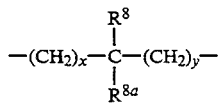

where
x and y are independently 0-1;
$R^8$ and $R^{8a}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^8$ and $R^{8a}$ can be taken together to form —(CH$_2$)$_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms;
and pharmaceutically acceptable salts thereof.

Still further preferred compounds of the instant invention are realized in the above structural formula when;
n is 0 or 1;
p is 0 to 2;
q is 1;
w is 1;
X is S(O)$_m$ or —CH=CH—;
m is 0 to 1;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, phenyl or substituted phenyl where the substituents are from 1 to 3 of halogen, $C_1$-$C_6$ alkyl, $C_1$-$C_6$ alkoxy, or hydroxy;
$R^{7a}$ and $R^{7b}$ are independently hydrogen, $C_1$-$C_6$ alkyl or substituted $C_1$-$C_6$ alkyl where the substituents are phenyl and v is 0 or 1;
$R^{3a}$ and $R^{3b}$ are independently hydrogen, $R^9$ or $C_1$-$C_6$ alkyl substituted with $R^9$;
$R^9$ is

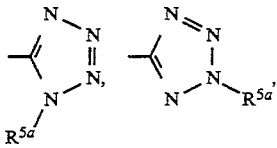

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{5b}$R$^{12b}$N(CH$_2$)$_v$—, R$^{5b}$R$^{12b}$NCO(CH$_2$)$_v$—, R$^{5b}$R$^{12c}$NN(R$^{12b}$)CO(CH$_2$)$_v$—, R$^{5b}$R$^{12b}$NCON(R$^{12a}$)(CH$_2$)$_v$—, R$^{5b}$R$^{12c}$NN(R$^{12b}$)CON(CH$_{12a}$)(CH$_2$)$_v$—, R$^{5b}$R$^{12c}$NN(R$^{12b}$)COO(CH$_2$)$_v$—, R$^{5b}$R$^{12b}$NCOO(CH$_2$)$_v$—, or R$^{13}$OCON(R$^{12a}$)(CH$_2$)$_v$—, where v is 0 to 2.

$R^{12a}$, $R^{12b}$ and $R^{12c}$ are independently $R^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2 and $R^1$ and $R^{10}$ are as defined.

$R^{13}$ is $C_1$-$C_6$ alkyl, substituted $C_1$-$C_6$ alkyl, where the substitutents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy.

$R^{10}$ and $R^{11}$ are independently hydrogen, $C_1$-$C_6$ alkyl or $C_1$-$C_5$ alkanoyl-$C_1$-$C_6$ alkyl;

$R^5$, $R^{5a}$ and $R^{5b}$ are independently hydrogen, $C_1$-$C_{10}$ alkyl or substituted $C_1$-$C_{10}$ alkyl where the substitutents are from 1 to 3 of hydroxy, $C_1$-$C_3$ alkoxy, fluoro, $R^1$, $R^2$ independently disubstituted phenyl, $C_1$-$C_{20}$ alkanoyloxy, $C_1$-$C_5$ alkoxycarbonyl or carboxy where $R^1$ and $R^2$ are as defined above;

$R^{15a}$ and $R^{15b}$ are independently hydrogen, hydroxy, halogen, —S(O)$_m$R$^{7a}$, R$^{12a}$R$^{12c}$N(CH$_2$)$_v$—, R$^{12a}$R$^{12b}$NCO(CH$_2$)$_v$—, $C_1$-$C_6$ alkoxy, phenyl, substituted phenyl, $C_1$-$C_6$ alkyl or substituted $C_1$-$C_6$ alkyl where the substitutents on the phenyl or alkyl are from 1 to 5 of hydroxy, $C_1$-$C_3$ alkoxy, $R^1$, $R^2$ independently disubstituted phenyl, $C_1$-$C_6$ alkanoyloxy, $C_1$-$C_5$ alkoxycarbonyl, carboxy or formyl where $R^1$, $R^2$, $R^{7a}$, $R^{12a}$, $R^{12b}$, $R^{12c}$, m and v are as defined;

$R^{16}$ is hydrogen, $C_1$-$C_6$ alkyl or substituted $C_1$-$C_6$ alkyl where the substitutents are from 1 to 3 of hydroxy, $C_1$-$C_6$ alkoxy, $R^1$, $R^2$ independently disubstituted phenyl, $C_1$-$C_5$ alkoxycarbonyl, carboxy or $C_1$-$C_5$ alkanoyl-$C_1$-$C_6$ alkyl where $R^1$ and $R^2$ are as defined;

$R^6$ is hydrogen;

A is

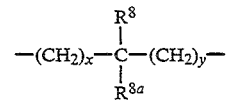

where
x and y are independently 0-1;
$R^8$ and $R^{8a}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, $R^1$, $R^2$ independently disubstituted phenyl, $C_1$-$C_5$ alkanoyloxy, $C_1$-$C_5$ alkoxycarbonyl or carboxy, where $R^1$, $R^2$, $R^{7a}$, and m are as defined; or $R^8$ and $R^{8a}$ can be taken together to form —(CH$_2$)$_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms;
and pharmaceutically acceptable salts thereof.

Representative preferred growth hormone releasing compounds of the present invention include the following:
1. N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;
2. N-[1-[[2'-[(Methylaminocarbonyl)amino][1,1'-biphenyl]-4-yl]-methyl]-2,3,4,5-tetrahydro-2-oxo-1H-1-benzazepin-3(R)-yl]-3-[(furan-2-yl)methyl]amino-3-methylbutanamide;

3. N-[1-[[2'-[(Morpholinocarbonyl)amino][1,1'-biphenyl]-4-yl]-methyl]-2,3,4,5-tetrahydro-2-oxo-1H-1-benzazepin-3(R)-yl]-3-[(furan-2-yl)methyl]amino-3-methylbutanamide;

4. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;

5. N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;

6. N-[1-[[2'-[(Methoxycarbonyl)amino][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

7. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

8. N-[1-[[2'-[(Methylaminocarbonyl)amino][1,1'-biphenyl]-4-yl]methyl]-7-trifluoromethyl-2,3,4,5-tetrahydro-2-oxo-1H-1-benzazepin-3(R)-yl]-3-[(furan-2-yl)methyl]amino-3-methylbutanamide;

9. N-[1-[[2'-[(Morpholinocarbonyl)amino][1,1'-biphenyl]-4-yl]methyl]-7-trifluoromethyl-2,3,4,5-tetrahydro-2-oxo-1H-1-benzazepin-3(R)-yl]-3-[(furan-2-yl)methyl]amino-3-methylbutanamide;

10. N-[1-[[2'-[[(2-Hydroxyethylamino)carbonyl]amino][1,1'-biphenyl]-4-yl]methyl]-7-trifluoromethyl-2,3,4,5-tetrahydro-2-oxo-1H-1-benzazepin-3(R)-yl]-3-[(furan-2-yl)methyl]amino-3-methylbutanamide;

11. N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

12. N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

13. 3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]-methyl]-2-oxo-1H-benzazepin-3(R)-yl]butanamide;

14. 3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-fluoro-2-oxo-1H-benzazepin-3(R)-yl]butanamide;

15. 3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-methoxy-2-oxo-1H-benzazepin-3(R)-yl]butanamide;

16. 3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-methylthio-2-oxo-1H-benzazepin-3(R)-yl]butanamide;

17. 3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-trifluoromethyl-2-oxo-1H-benzazepin-3(R)-yl]butanamide;

18. 3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]butanamide;

19. 3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-fluoro-2-oxo-1H-benzazepin-3(R)-yl]butanamide;

20. 3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-methoxy-2-oxo-1H-benzazepin-3(R)-yl]butanamide;

21. 3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-methylthio-2-oxo-1H-benzazepin-3(R)-yl]butanamide;

22. 3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-trifluoromethyl-2-oxo-1H-benzazepin-3(R)-yl]butanamide;

23. 3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]butanamide;

24. 3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-fluoro-2-oxo-1H-benzazepin-3(R)-yl]butanamide;

25. 3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-methoxy-2-oxo-1H-benzazepin-3(R)-yl]butanamide;

26. 3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-methylthio-2-oxo-1H-benzazepin-3(R)-yl]butanamide;

27. 3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-trifluoromethyl-2-oxo-1H-benzazepin-3(R)-yl]butanamide;

28. 3-[(Furan-2-yl)methyl]amino-3-methyl-N-[2,3,4,5-tetrahydro-1-[[2'-[[[[(hydroxyethyl)amino]carbonyl]amino]methyl][1,1'-biphenyl]-4-yl]methyl]-2-oxo-1H-benzazepin-3(R)-yl]butanamide;

29. 3-[(Furan-2-yl)methyl]amino-3-methyl-N-[2,3,4,5--tetrahydro-1-[[2'-[[[[(hydroxyethyl)amino]carbonyl]amino]methyl][1,1'-biphenyl]-4-yl]methyl]-7-fluoro-2-oxo-1H-benzazepin-3(R)-yl]butanamide;

30. 3-[(Furan-2-yl)methyl]amino-3-methyl-N-[2,3,4,5--tetrahydro-1-[[2'-[[[[(hydroxyethyl)amino]carbonyl]amino]methyl][1,1'-biphenyl]-4-yl]methyl]-7-methoxy-2-oxo-1H-benzazepin-3(R)-yl]butanamide;

31. 3-[(Furan-2-yl)methyl]amino-3-methyl-N-[2,3,4,5-tetrahydro-1-[[2'-[[[[(hydroxyethyl)amino]carbonyl]amino]methyl][1,1'-biphenyl]-4-yl]methyl]-7-methylthio-2-oxo-1H-benzazepin-3(R)-yl]butanamide;

32. 3-[(Furan-2-yl)methyl]amino-3-methyl-N-[2,3,4,5-tetrahydro-1-[[2'-[[[[(hydroxyethyl)amino]carbonyl]amino]methyl][1,1'-biphenyl]-4-yl]methyl]-7-trifluoromethyl-2-oxo-1H-benzazepin-3(R)-yl]butanamide;

33. 3-[(Furan-2-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide;

34. 3-[(Furan-2-yl)methyl]amino-3-methyl-N-[2,3,4,5-tetrahydro-6-fluoro-2-oxo-1-[[2'-(1H-tetrazol-5-yl)[1,1'-biphenyl]-4-yl]methyl]-1H-1-benzazepin-3(R)-yl]butanamide;

35. 3-[(Furan-2-yl)methyl]amino-3-methyl-N-[2,3,4,5-tetrahydro-7-fluoro-2-oxo-1-[[2'-(1H-tetrazol-5-yl)[1,1'-biphenyl]-4-yl]methyl]-1H-1-benzazepin-3(R)-yl]butanamide;

36. 3-[(Furan-2-yl)methyl]amino-3-methyl-N-[2,3,4,5-tetrahydro-7-trifluoromethyl-2-oxo-1-[[2'-(1H-tetrazol-5-yl)[1,1'-biphenyl]-4-yl]methyl]-1H-1-benzazepin-3(R)-yl]butanamide;
37. 3-[(Furan-2-yl)methyl]amino-3-methyl-N-[2,3,4,5-tetrahydro-7-methylthio-2-oxo-1-[[2'-(1H-tetrazol-5-yl)[1,1'-biphenyl]-4-yl]methyl]-1H-1-benzazepin-3(R)-yl]butanamide;
38. 3-[(Furan-2-yl)methyl]amino-3-methyl-N-[2,3,4,5-tetrahydro-7-methoxy-2-oxo-1-[[2'-(1H-tetrazol-5-yl)[1,1'-biphenyl]-4-yl]methyl]-1H-1-benzazepin-3(R)-yl]butanamide;
39. 4'-[[3(R)-[[3-[(Furan-2-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;
40. 4'-[[3(R)-[[3-[(Furan-2-yl)methyl]amino-3-methyl-1-oxobutyl]amino]-7-fluoro-2,3,4,5-tetrahydro-2-oxo-1H-1-benzazepin-1-yl]methyl][1,1'-biphenyl]-2-carboxamide;
41. 4'-[[3(R)-[[3-[(Furan-2-yl)methyl]amino-3-methyl-1-oxobutyl]amino]-7-trifluoro-2,3,4,5-tetrahydro-2-oxo-1H-1-benzazepin-1-yl]methyl][1,1'-biphenyl]-2-carboxamide;
42. 4'-[[3(R)-[[3-[(Furan-2-yl)methyl]amino-3-methyl-1-oxobutyl]amino]-7-methylthio-2,3,4,5-tetrahydro-2-oxo-1H-1-benzazepin-1-yl]methyl][1,1'-biphenyl]-2-carboxamide;
43. 4'-[[3(R)-[[3-[(Furan-2-yl)methyl]amino-3-methyl-1-oxobutyl]amino]-7-methoxy-2,3,4,5-tetrahydro-2-oxo-1H-1-benzazepin-1-yl]methyl][1,1'-biphenyl]-2-carboxamide;
44. N-Ethyl-4'-[[3(R)-[[3-[(furan-2-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;
45. N-Ethyl-4'-[[3(R)-[[3-[(furan-2-yl)methyl]amino-3-methyl-1-oxobutyl]amino]-7-fluoro-2,3,4,5-tetrahydro-2-oxo-1H-1-benzazepin-1-yl]methyl][1,1'-biphenyl]-2-carboxamide;
46. N-Ethyl-4'-[[3(R)-[[3-[(furan-2-yl)methyl]amino-3-methyl-1-oxobutyl]amino]-7-trifluoromethyl-2,3,4,5-tetrahydro-2-oxo-1H-1-benzazepin-1-yl]methyl][1,1'-biphenyl]-2-carboxamide;
47. N-Ethyl-4'-[[3(R)-[[3-[(furan-2-yl)methyl]amino-3-methyl-1-oxobutyl]amino]-7-methylthio-2,3,4,5-tetrahydro-2-oxo-1H-1-benzazepin-1-yl]methyl][1,1'-biphenyl]-2-carboxamide;
48. N-Ethyl-4'-[[3(R)-[[3-[(furan-2-yl)methyl]amino-3-methyl-1-oxobutyl]amino]-7-methoxy-2,3,4,5-tetrahydro-2-oxo-1H-1-benzazepin-1-yl]methyl][1,1'-biphenyl]-2-carboxamide;
49. 3-[(Furan-2-yl)methyl]amino-3-methyl-N-[2,3,4,5-tetrahydro-2-oxo-1-[[2'-hydroxymethyl[1,1'-biphenyl]-4-yl]methyl]-1H-1-benzazepin-3(R)-yl]butanamide;
50. 3-[(Furan-2-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;
51. 3-[(Furan-2-yl)methyl]amino-3-methyl-N-[8-fluoro-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;
52. 3-[(Furan-2-yl)methyl]amino-3-methyl-N-[8-trifluoromethyl-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;
53. 3-[(Furan-2-yl)methyl]amino-3-methyl-N-[8-methylthio-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;
54. 4'-[[3(S)-[[3-[(Furan-2-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;
55. N-Ethyl-4'-[[3(S)-[[3-[(Furan-2-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;
56. N-[5-[[2'-[(Methoxycarbonyl)amino][1,1'-biphenyl]-4-yl]methyl]-2,3,4,5-tetrahydro-4-oxo-1,5-benzothiazepin-3(S)-yl]-3-[(furan-2-yl)methyl]amino-3-methylbutanamide;
57. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[(furan-2-yl)methyl]amino-3-methylbutanamide;
58. N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-[(furan-2-yl)methyl]amino-3-methylbutanamide;
59. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[(furan-2-yl)methyl]amino-3-methylbutanamide;
60. 3-[(Furan-2-yl)methyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;
61. 3-[(Furan-2-yl)methyl]amino-3-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]butanamide;
62. 3-[(Furan-2-yl)methyl]amino-3-methyl-N-[2,3,4,5-tetrahydro-5-[[2'-[[[(methylamino)carbonyl]amino]methyl][1,1'-biphenyl]-4-yl]methyl]-8-methoxy-4-oxo-1,5-benzothiazepin-3(S)-yl]butanamide;
63. 3-[(Furan-2-yl)methyl]amino-3-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]butanamide;
64. 3-[(Furan-2-yl)methyl]amino-3-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]butanamide;
65. 3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]4-oxo-1,5-benzothiazepin-3(S)-yl]butanamide;
66. 3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;
67. 3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]butanamide;
68. 3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;
69. 3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]butanamide;

70. 3-[(Furan-2-yl)methyl]amino-3-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]butanamide;

71. 3-[(Furan-2-yl)methyl]amino-3-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]butanamide;

72. 3-[(Furan-2-yl)methyl]amino-3-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]butanamide;

73. 3-[(Furan-2-yl)methyl]amino-3-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]butanamide;

74. 3-[(Furan-2-yl)methyl]amino-3-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzothiazepin-3(S)-yl]butanamide;

75. 3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]butanamide;

76. 3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-fluoro-4-oxo-1,5-benzothiazepin-3(S)-yl]butanamide;

77. 3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-methoxy-4-oxo-1,5-benzothiazepin-3(S)-yl]butanamide;

78. 3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-methylthio-4-oxo-1,5-benzothiazepin-3(S)-yl]butanamide;

79. 3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]butanamide;

80. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[(oxazol-5-yl)methyl]amino-3-methylbutanamide;

81. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[(oxazol-5-yl)methyl]amino-3-methylbutanamide;

82. 3-[(Oxazol-5-yl)methyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;

83. 3-[(Oxazol-5-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide;

84. N-Ethyl-4'-[[3(R)-[[3-[(oxazol-5-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;

85. 3-[(Oxazol-5-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

86. N-Ethyl-4'-[[3(S)-[[3-[(oxazol-5-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;

87. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[(oxazol-5-yl)methyl]amino-3-methylbutanamide;

88. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[(oxazol-5-yl)methyl]amino-3-methylbutanamide;

89. 3-[(Oxazol-5-yl)methyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;

90. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[((benzofuran-2-yl)methyl]amino-3-methylbutanamide;

91. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[(benzofuran-2-yl)methyl]amino-3-methylbutanamide;

92. 3-[(Benzofuran-2-yl)methyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;

93. 3-[(Benzofuran-2-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide;

94. N-Ethyl-4'-[[3(R)-[[3-[(benzofuran-2-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;

95. 3-[(Benzofuran-2-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

96. N-Ethyl-4'-[[3(S)-[[3-[(benzofuran-2-yl)methyl]amino-3-methyl-1-oxobutyl]amino-2,3,4,5-tetrahydro-4-oxo-1,5-benzothiazepin-5(2H)-yl]methyl][1,1'-biphenyl]-2-carboxamide;

97. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[(benzofuran-2-yl)methyl]amino-3-methylbutanamide;

98. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[(benzofuran-2-yl)methyl]amino-3-methylbutanamide; and 99. 3-[(Benzofuran-2-yl)methyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide.

Representative examples of the nomenclature employed are given below:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[(imidazol-2-yl)methyl]amino-3-methylbutanamide

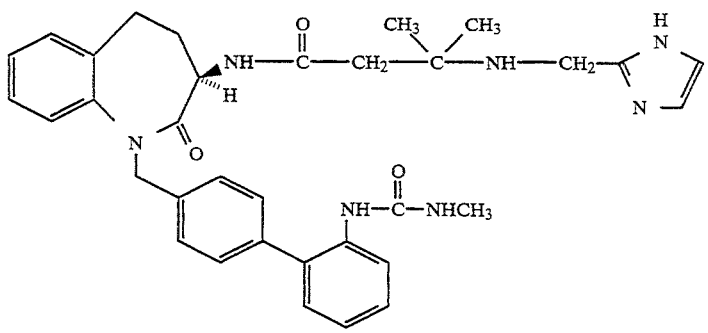

N-Ethyl-4'-[[3(R)-[[2-[(furan-2-yl)methyl]amino-2-methyl-1-oxopropyl]amino]-2,3,4,5-tetrahydro-2-oxo-1H-1-benzazepin-1-yl]methyl][1,1'-biphenyl]-2-carboxamide 3-[(Benzofuran-2-yl)methyl]amino-3-methyl-N-[2,3,4,5-tetrahydro-5-[[2'-[2-[[4-morpholinocarbonyl]amino]ethyl][1,1'-biphenyl]-4-yl]methyl]-4-oxo-1,5-benzothiazepin-3(S)-yl]butanamide

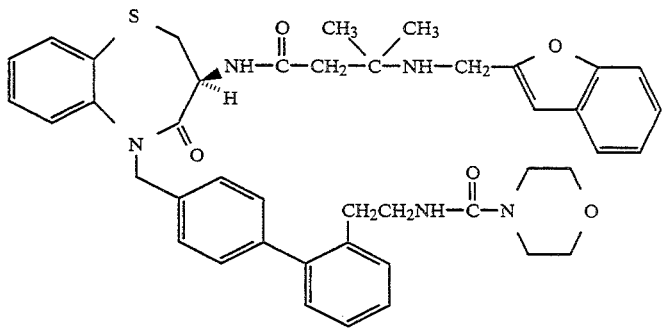

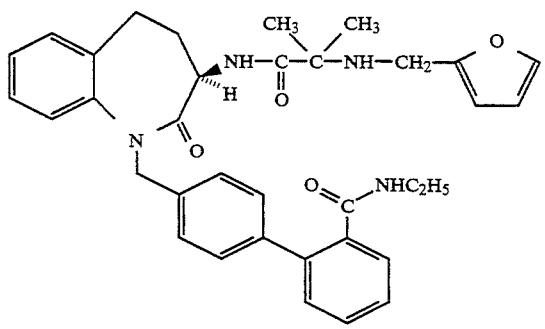

3-[(Oxazol-5-yl)methyl]amino-3-methyl-N-[7-methyl-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when $n=0$, the asymmetric center is designated as the R-isomer. When $n=1$, this center will be

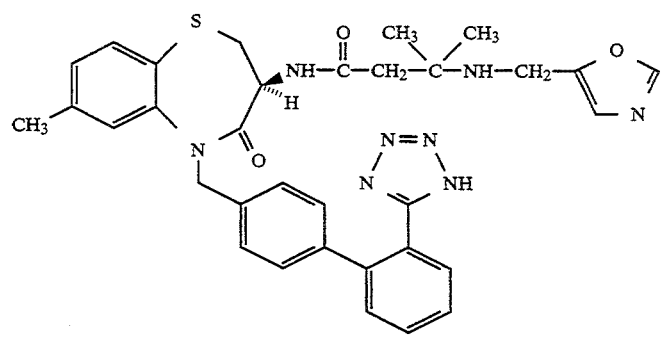

designated according to the R/S rules as either R or S depending upon the value of X.

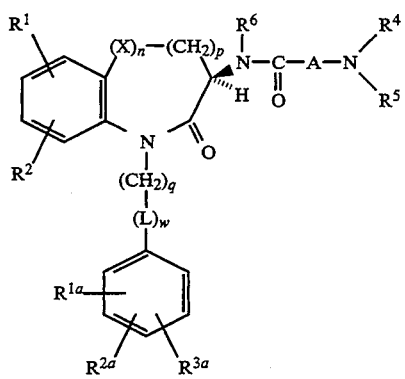

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a tetrazole or carboxy can be isolated in the form of their inorganic salt in which the counterion can be selected from sodium, potassium, lithium, calcium, magnesium and the like, as well as from organic bases.

The compounds (I) of the present invention are derived from intermediates such as those of formula II. The preparation of compounds of formula II wherein $R^{3a}$ or $R^{3b}$ is tetrazole or $R^{7b}OCO(CH_2)_v$— has been previously described by Fisher, et al, U.S. Pat. No. 5,206,235 and references cited therein. The preparation of other compounds of formula II is described in the following reaction schemes.

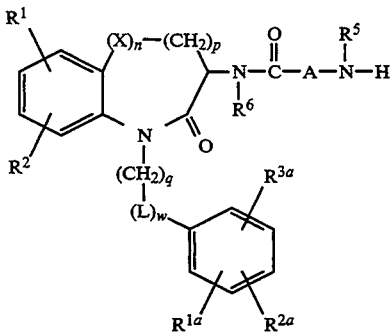

Compounds of formula II are prepared by alkylation of intermediates of formula III as shown in Scheme 1. The preparation of compounds of formula III has also been previously described by Fisher, et al, U.S. Pat. No. 5,206,235 and references cited therein. Alkylation of intermediates of formula III is conveniently carried out in anhydrous dimethyl formamide (DMF) in the presence of bases such as sodium hydride or potassium t-butoxide for a period of 0.5 to 24 hours at temperatures of 20°–100° C., with an alkylating agent IV, wherein Y is a good leaving group such as Cl, Br, I, O-methanesulfonyl or O-(p-toluenesulfonyl). Substituents on the alkylating agent IV may need to be protected during alkylation. A description of such protecting groups may be found in: *Protective Groups in Organic Synthesis*, T. W. Greene, John Wiley and Sons, New York, 1981.

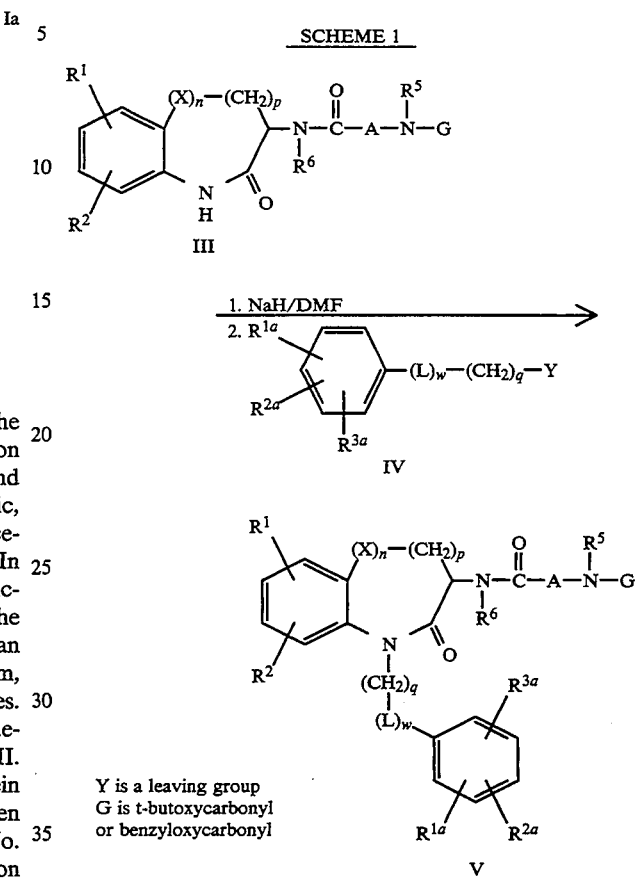

Alkylating agents IV are in some cases commercially available or may be prepared by methods described in the literature and familiar to one skilled in the art. Intermediates of formula II where $R^{3a}$ or $R^{3b}$ is a carbamate, semicarbazide or urea derivative, wherein this functionality is attached to the phenyl ring by a nitrogen atom are prepared from intermediate 1, obtained by alkylation with a derivative of formula IV wherein $R^{3a}$ or $R^{3b}$ is a nitro group as shown in Scheme 2.

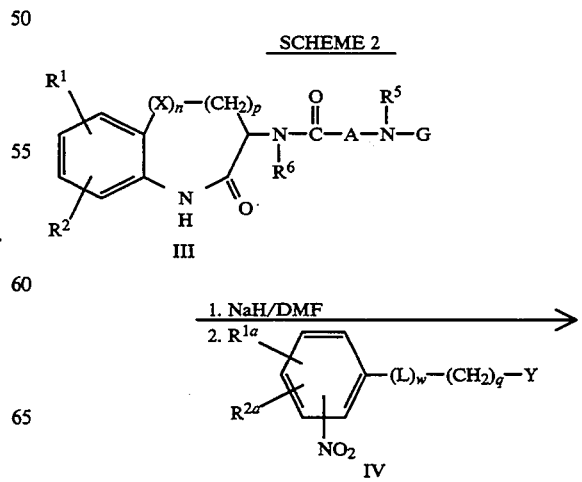

-continued
SCHEME 2

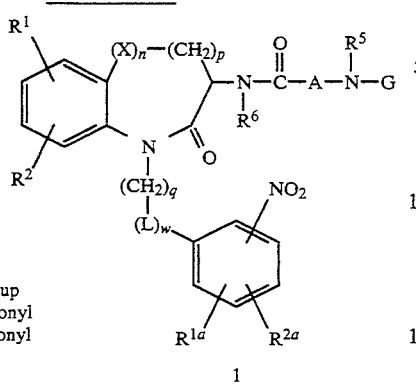

Y is a leaving group
G is t-butoxycarbonyl
or benzyloxycarbonyl

A useful method of synthesizing a preferred alkylating agent 5 is shown in reaction Scheme 3.

SCHEME 3

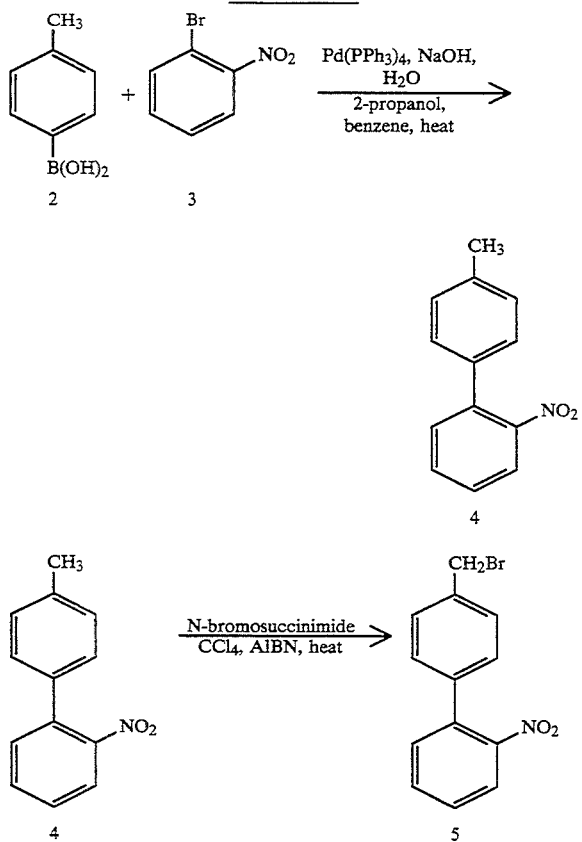

Reaction of 4-tolylboronic acid 2 with 2-bromonitrobenzene 3 in the presence of a transition metal catalyst such as (tetrakis)triphenylphosphine palladium (0) in a mixed solvent system containing aqueous sodium hydroxide, water, 2-propanol and benzene at elevated temperatures for several hours gives the coupled product 4 in good overall yield. Chromatographic purification and separation of unwanted by-products is conveniently performed on silica, eluting with common organic solvents such as hexane, ethyl acetate and methylene chloride. Conversion of 4 to the bromide derivative 5 is accomplished by treatment with N-bromosuccinimide in refluxing carbon tetrachloride in the presence of a radical initiator such as benzoyl peroxide or 2,2'-azobisisobutyronitrile (AIBN).

As shown in Scheme 4, reduction of the nitro group of 1 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 1 must be compatible with the experimental conditions anticipated for reduction. For example, intermediate 1 wherein G is t-butoxycarbonyl (BOC) is stable to the conditions of catalytic reduction employed in the conversion to 6. Intermediate 6 may also be further elaborated to a new intermediate 7 by reductive alkylation carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 4

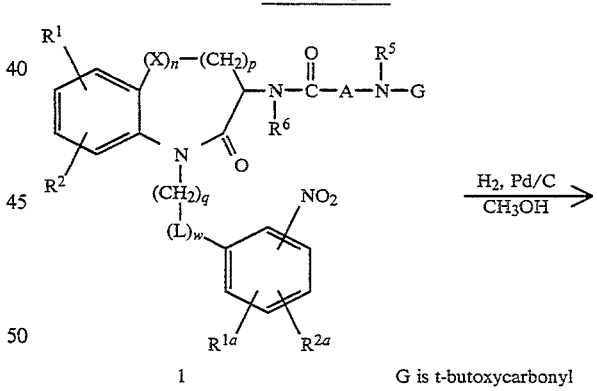

G is t-butoxycarbonyl

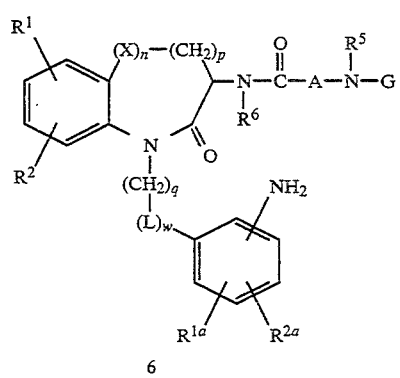

-continued
SCHEME 4

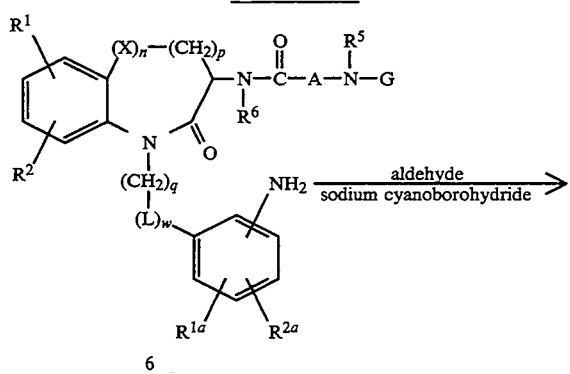

6

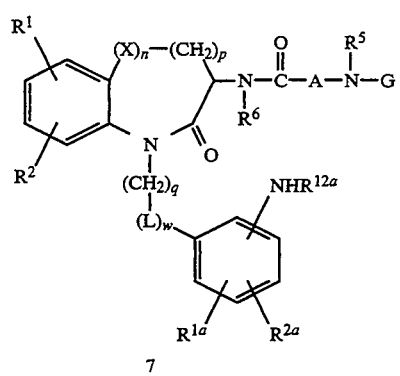

7

Elaboration of 7 to carbamate compound 8 is achieved by reaction with the appropriate chloroformate reagent in pyridine or in methylene chloride with triethylamine as shown in Scheme 5.

SCHEME 5

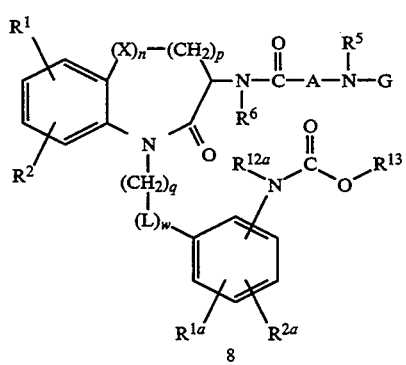

8

Transformation of amine intermediate 7 to urea derivatives is accomplished in several ways. Terminally disubstituted compounds 10 can be obtained directly by reaction of 7 with a disubstituted carbamoyl chloride 9 in an inert solvent such as methylene chloride in the presence of triethylamine or 4-dimethylaminopyridine. In addition, mono-substituted compound 12 wherein either $R^{5b}$ or $R^{12b}$ is hydrogen is obtained from 7 by reaction with an isocyanate 11 as shown in Scheme 6. Terminally unsubstituted urea 12, wherein $R^{12b}$ is hydrogen, is also prepared from amine 7 by reaction with trimethylsilyl isocyanate (11; $R^{12b}$ is $(CH_3)_3Si$).

SCHEME 6

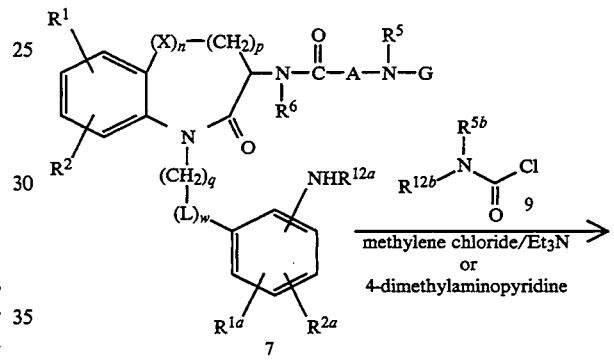

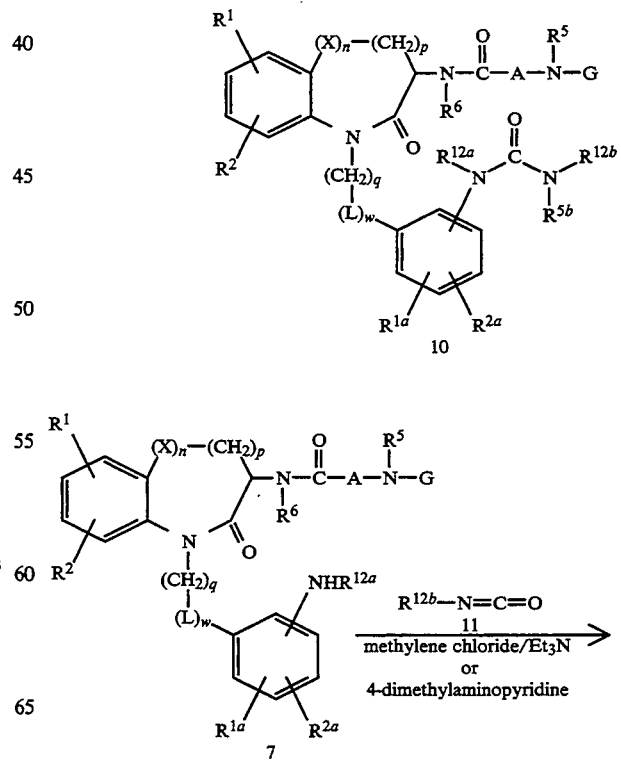

10

-continued
SCHEME 6

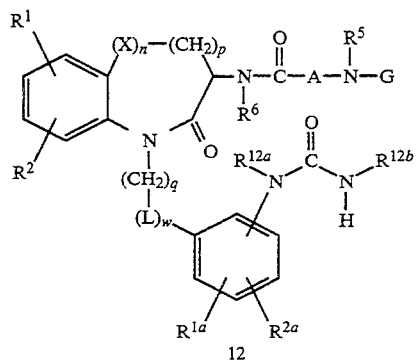
12

Alternatively, amine 6 is converted to an isocyanate 13 by treatment with phosgene or an equivalent reagent such as bis(trichloromethyl)carbonate (triphosgene) as indicated in Scheme 7. Subsequent reaction of 13 with primary or secondary amines in an inert solvent such as methylene chloride gives the corresponding urea derivative 10 in good yield. Isocyanate 13 is also converted to substituted semicarbazides 14 or hydroxy- or alkoxyureas 15 by reaction with substituted hydrazines or hydroxy- or alkoxylamines, respectively.

SCHEME 7

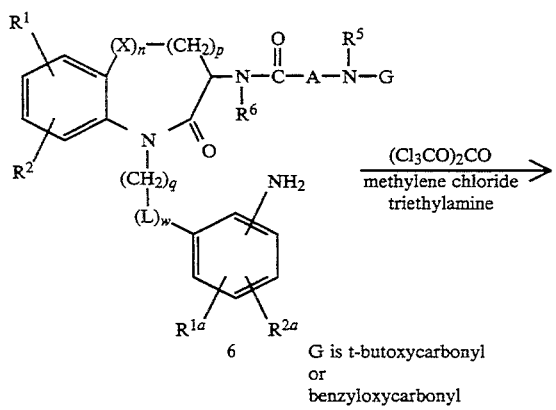
6  G is t-butoxycarbonyl
or
benzyloxycarbonyl

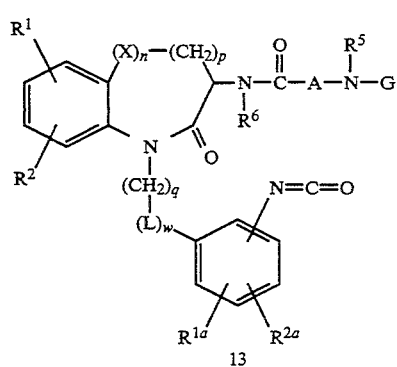
13

-continued
SCHEME 7

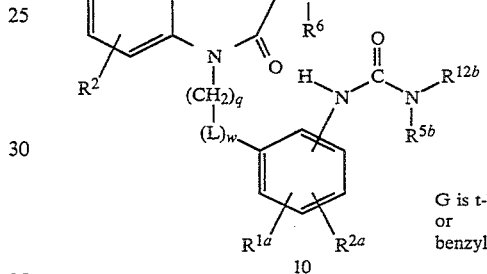

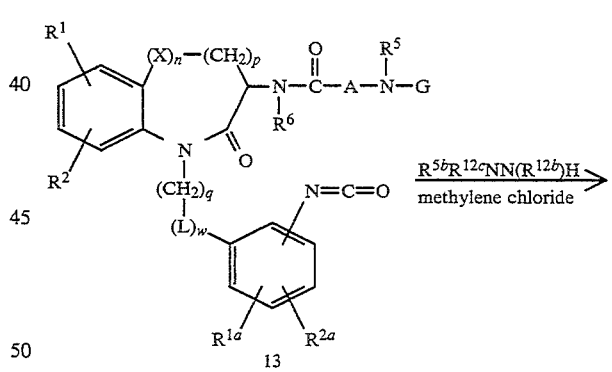
10  G is t-butoxycarbonyl
or
benzyloxycarbonyl

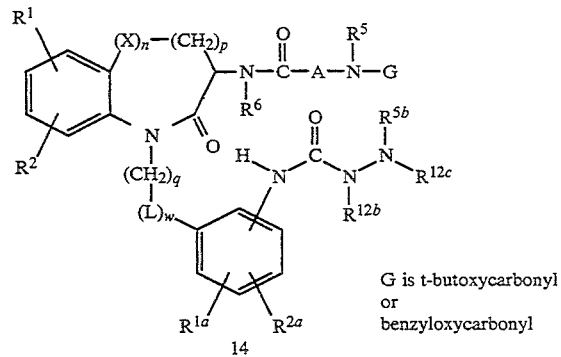
14  G is t-butoxycarbonyl
or
benzyloxycarbonyl

-continued
SCHEME 7

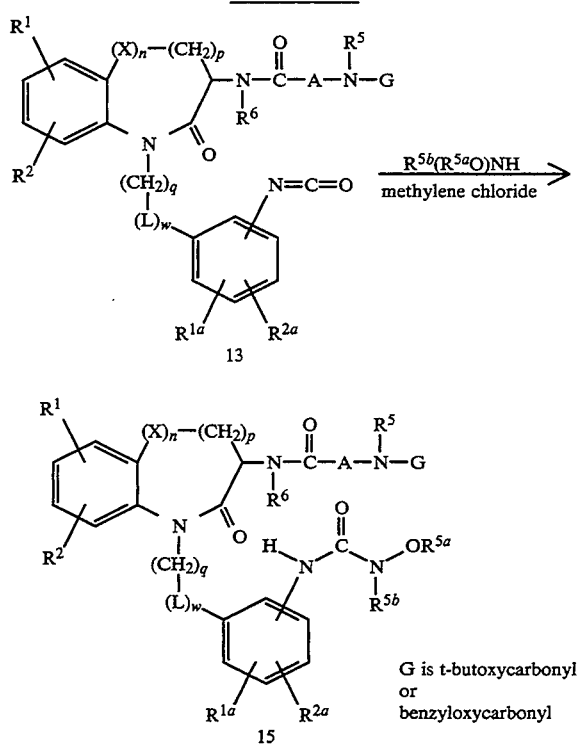

15

Intermediates of formula II where $R^{3a}$ or $R^{3b}$ is a carbazate or carbamate derivative where attachment to the phenyl ring is through the oxygen atom of the carbazate or carbamate linkage are prepared from acetophenone intermediate 16 as indicated in Scheme 8.

SCHEME 8

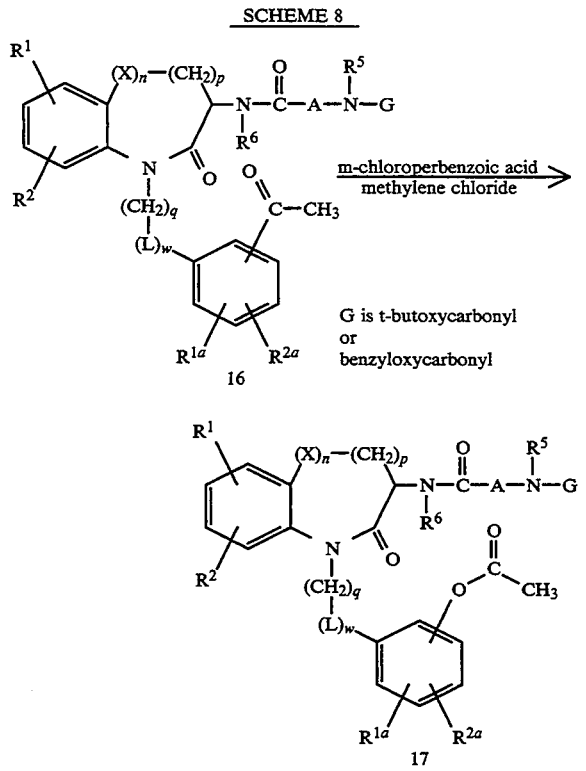

-continued
SCHEME 8

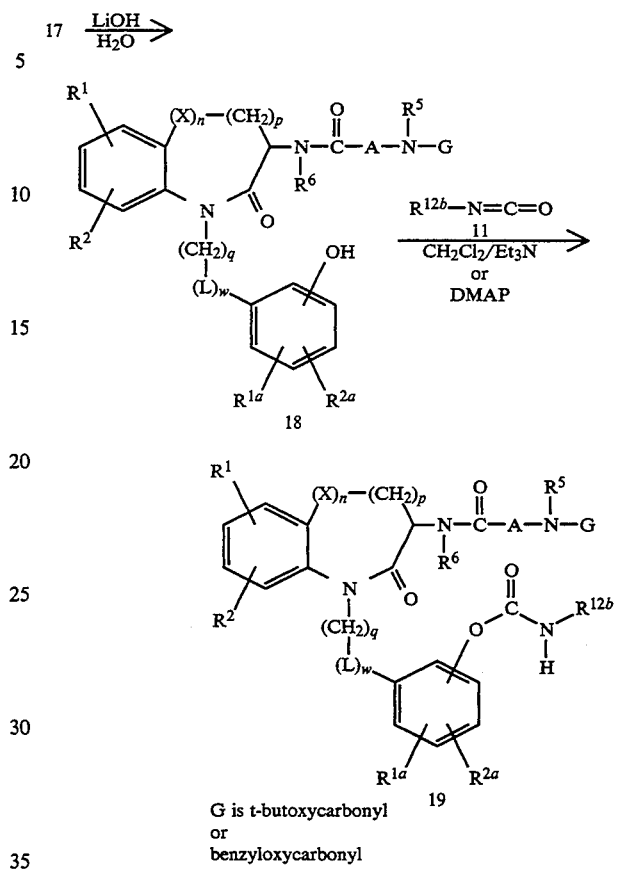

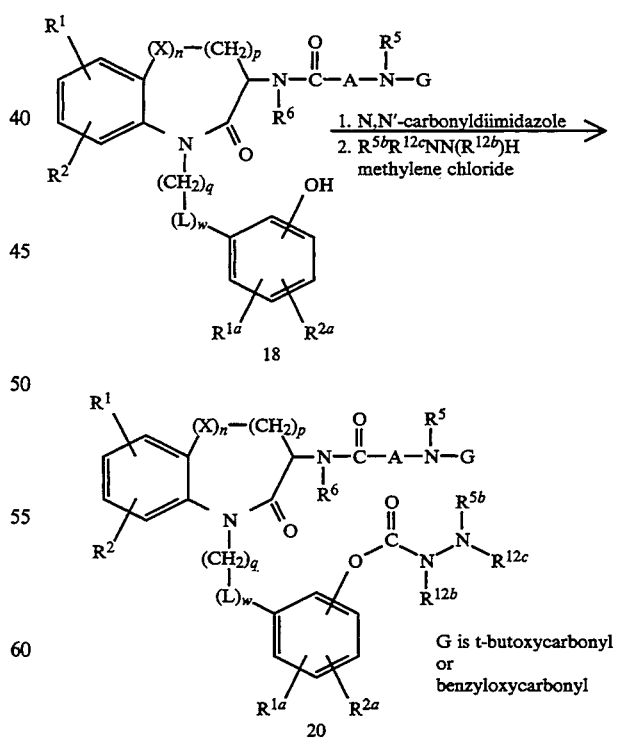

Oxidative rearrangement of 16 through the use of a peroxy-carboxylic acid (Baeyer-Villager reaction) such as m-chloroperbenzoic acid gives the ester 17 which is hydrolyzed in the presence of a strong base such as sodium or lithium hydroxide to give phenol 18. Reaction of 18 with an isocyanate leads directly to carbamate 19. Additionally, treatment of 18 with N,N'-carbonyldiimidazole in dimethylformamide can form an activated intermediate which will react with substituted hydrazine reagents to give a carbazate product 20.

Intermediates of formula II wherein $R^{3a}$ or $R^{3b}$ is $R^{5b}R^{12b}NCON(R^{12a})CH_2-$, $R^{5b}R^{12b}NCSN(R^{12a})CH_2-$, $R^{5b}R^{12c}NN(R^{12b})CSN(R^{12a})CH_2-$, $R^{5b}R^{12c}NN(R^{12b})CON(R^{12a})CH_2-$ or $R^{13}OCON(R^{12a})CH_2-$ can be prepared from the t-butyl ester intermediate 21 as described in Scheme 9. Removal of the t-butyl ester through the use of trifluoroacetic acid will give the carboxylic acid 22. It may be appreciated by one skilled in the art that the protecting group G in 21 must therefore be compatible with the strongly acidic conditions employed for ester cleavage; hence G is taken as benzyloxycarbonyl. Conversion of the carboxylic acid to the benzylamine derivative 23 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 23 can be further elaborated to 24 by the aforementioned reductive amination procedure.

SCHEME 9

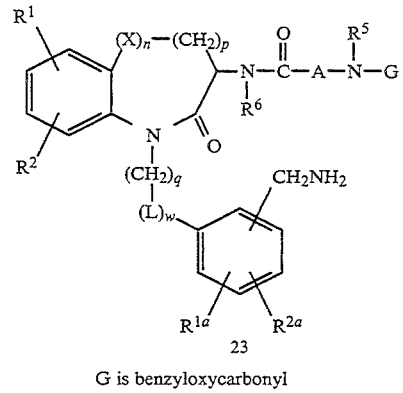

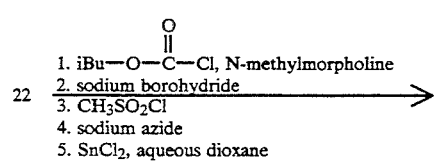

Reactions of amine 24 with the appropriate reagents to form urea-linked compounds 25 and 26 and carbamate-linked compound 27 are illustrated in Scheme 10. Terminally unsubstituted urea 25, wherein $R^{12b}$ is hydrogen, is also prepared from amine 24 by reaction with trimethylsilyl isocyanate (11; $R^{12b}$ is $(CH_3)_3Si$).

SCHEME 10
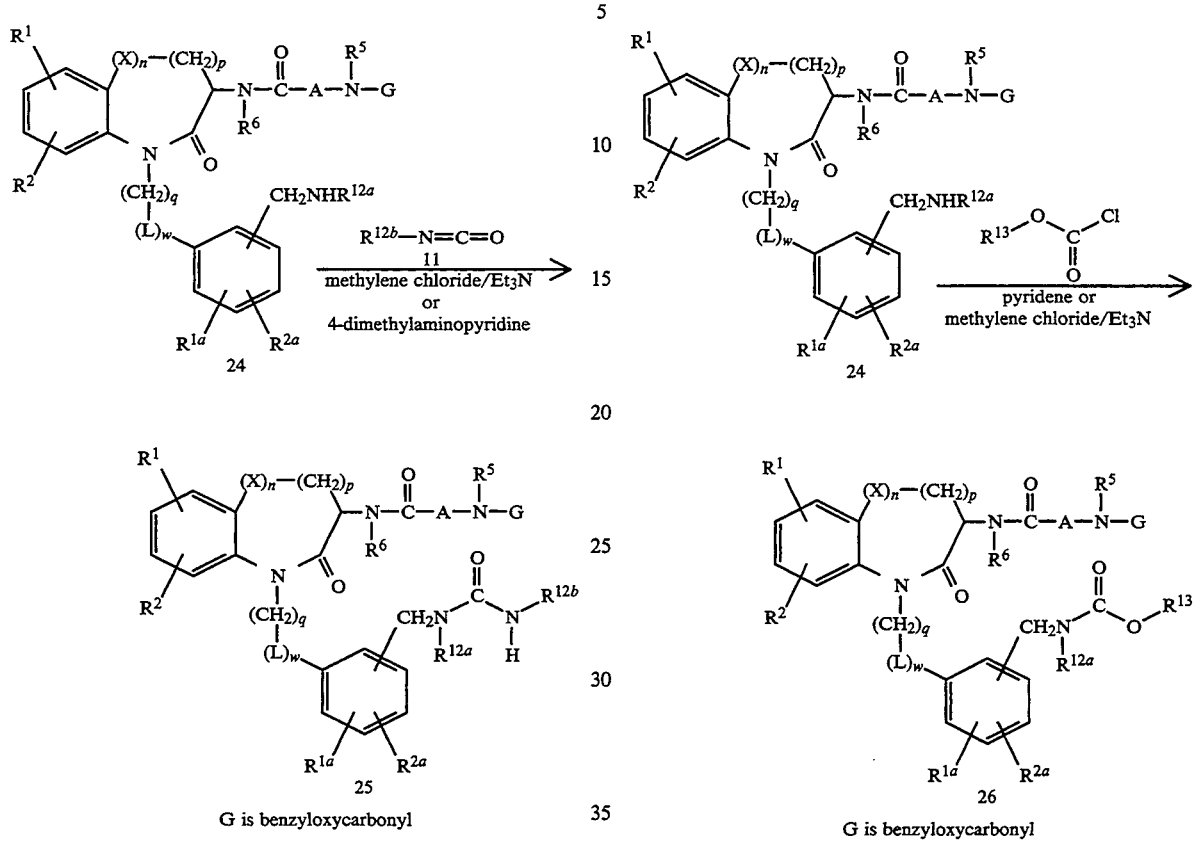
G is benzyloxycarbonyl
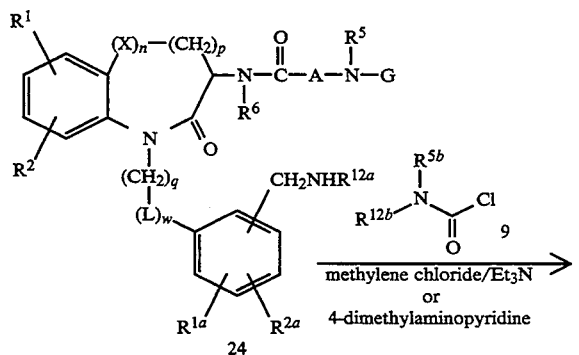
As shown in Scheme 11, hydrazide compound 27 can be prepared from intermediate 24 by a two-step procedure consisting of activation of the amine via treatment with N,N'-carbonyldiimidazole followed by treatment with the appropriately substituted hydrazine derivative $R^{5b}R^{12c}NN(R^{12b})H$.
SCHEME 11
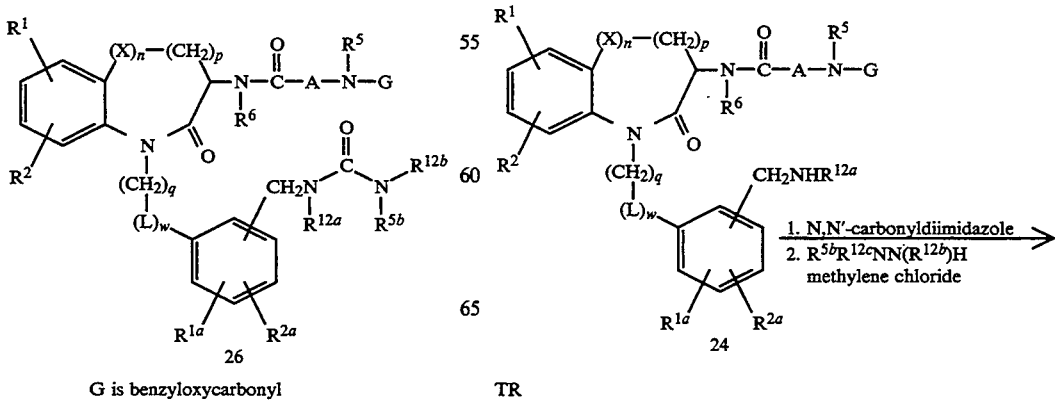

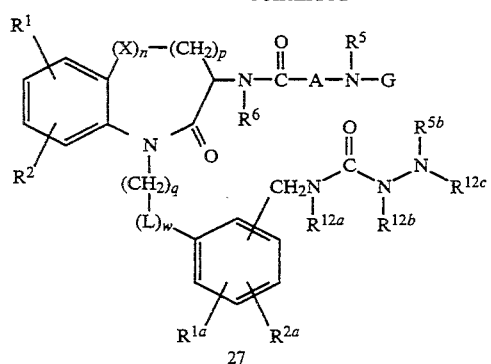

G is benzyloxycarbonyl

A useful preparation of the protected benzylamine intermediate 32 is shown in Scheme 12. Metallation of 4-bromobenzyl t-butyldiphenylsilylether 28 with n-butyllithium followed by treatment with triisopropyl borate gives the aryl boronic acid 29. Reaction of 29 with 2-bromo-N-(t-butoxycarbonyl)benzylamine 30 in the presence of tetrakis(triphenylphosphine)palladium(0) and sodium hydroxide in a mixed solvent system at elevated temperature gives the coupled product 31 in good yield. Desilylation and conversion to the O-methanesulfonate 32 is achieved by treatment with tetrabutylammonium fluoride followed by methanesulfonyl chloride. Reaction of 32 with compounds of formula III is carried out using the conditions described in Scheme 1.

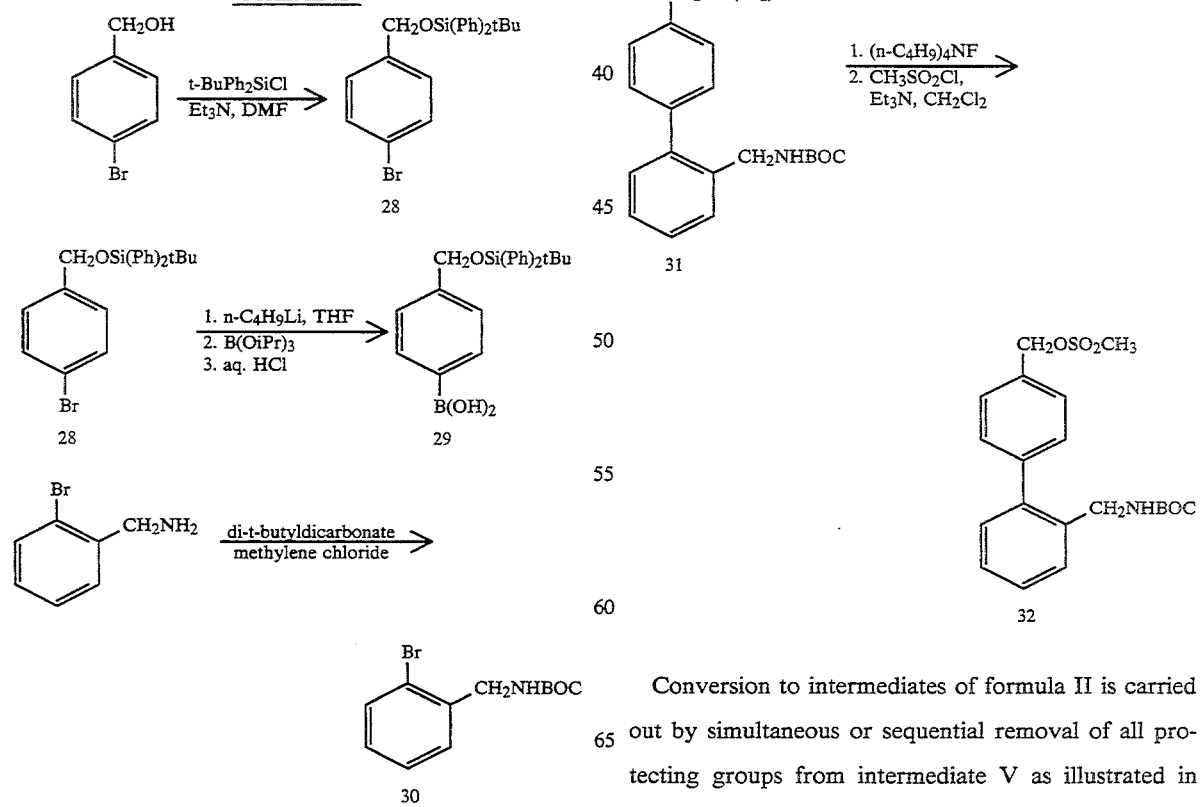

SCHEME 12

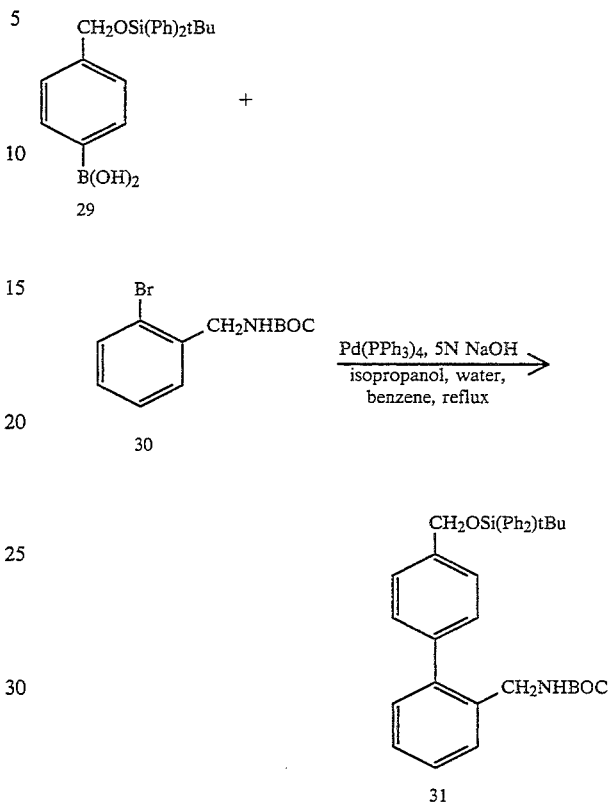

Conversion to intermediates of formula II is carried out by simultaneous or sequential removal of all protecting groups from intermediate V as illustrated in Scheme 13.

SCHEME 13

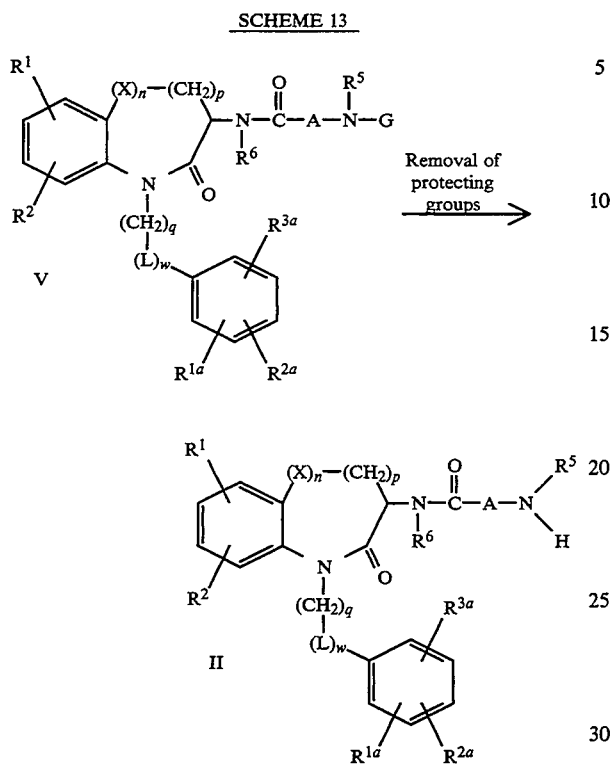

Removal of benzyloxycarbonyl (CBz) groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, New York. 1981.

As shown in Scheme 14, intermediates of formula II are elaborated to compounds of formula I by reductive alkylation with an aldehyde by the aforementioned procedures. The products, obtained as hydrochloride or trifluoroacetate salts, are conveniently purified by reverse phase high performance liquid chromatography (HPLC) or by recrystallization.

SCHEME 14

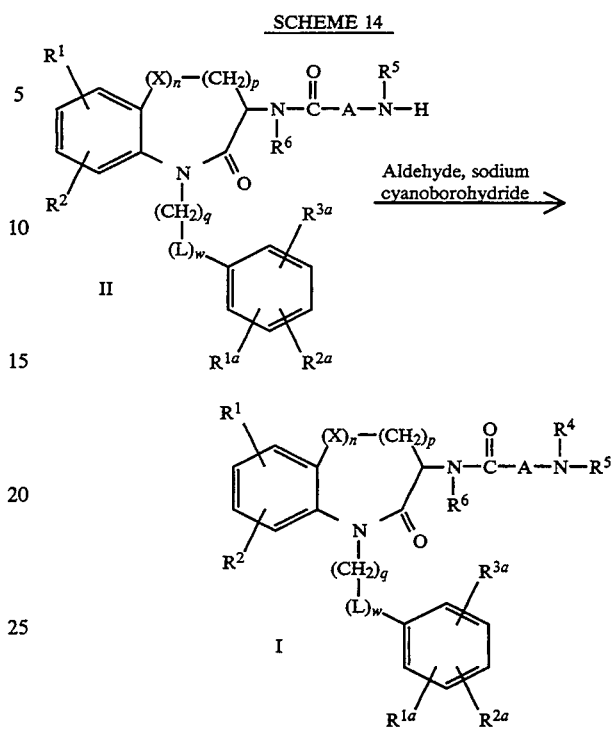

Compounds of formula I wherein $R^4$ is taken as $C_1$-$C_{10}$ alkyl substituted with $R^{14}$ are prepared from intermediate II by the aforementioned reductive amination procedure using an aldehyde appropriately substituted with the heterocycle, $R^{14}$. For example, as shown in Scheme 15, compounds of formula I wherein $R^4$ is —$CH_2R^{14}$ are conveniently prepared using the aldehyde, $R^{14}$—CHO (33) and the reducing agent, sodium cyanoborohydride.

SCHEME 15

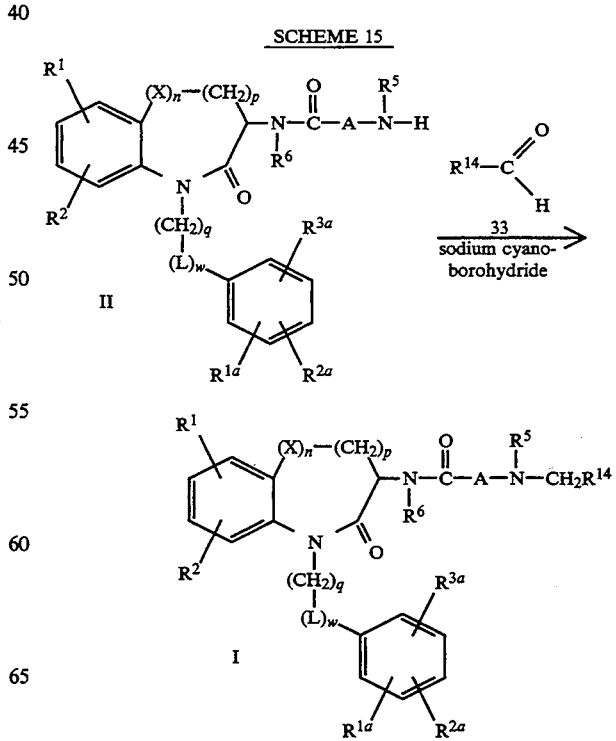

A route to the sub-class of compounds of formula I that can be described by formula VII is shown in Scheme 16.

SCHEME 16

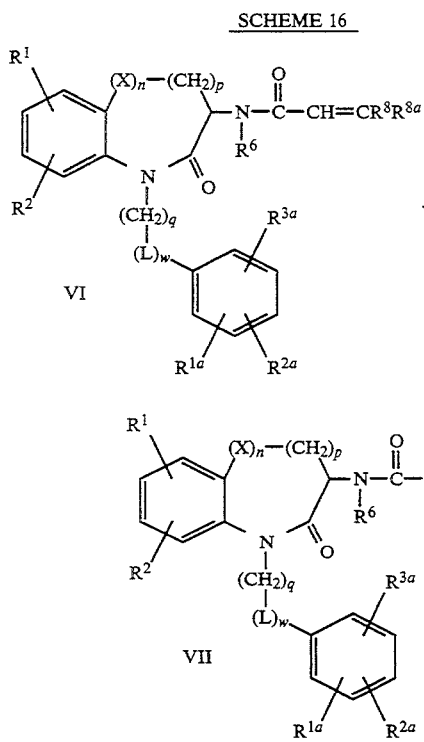

Thus, intermediates of formula VI are reacted with $R^{14}$—$NH_2$ neat or in a polar solvent such as dimethylsulfoxide at temperatures of 50° C. to 200° C., to give compounds of formula VII. Intermediates of formula VI may themselves be prepared by the transformations described by Fisher, et al, U.S. Pat. No. 5,206,235 and references cited therein.

It should be appreciated by one skilled in the art that the order of the alkylation step (Scheme 1) and the reductive alkylation step (Scheme 14) may be reversed to facilitate the reaction or to avoid unwanted reaction products. Thus, as demonstrated in Scheme 16, intermediate III is deprotected using the aforementioned conditions, and the resulting amine intermediate VIII is reacted with the appropriate aldehyde under the reductive alkylation conditions described previously. The new intermediate thus obtained (IX), may then be treated with alkylating agent IV following the procedures described in Scheme 1 to give, after removal of any protecting groups, compounds of formula I.

SCHEME 16

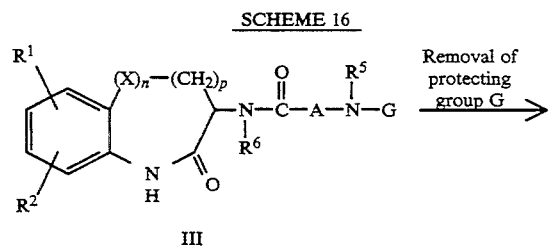

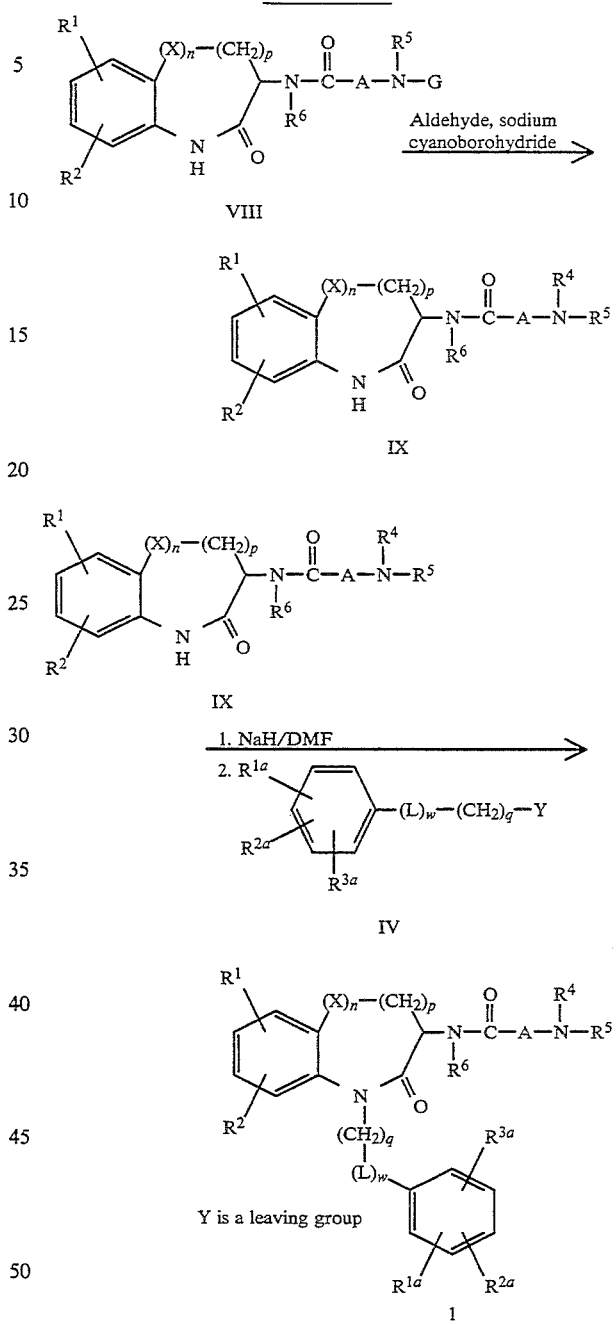

It is again noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity.

For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For s example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A further use of the disclosed novel benzo-fused lactam growth hormone secretagogues is in combination with other growth hormone secretagogues such as GHRP-6, GHRP-1 or GHRP-2 as described in U.S. Pat. No. 4,411,890; and publications WO 89/07110 and WO 89/07111 and B-HT 920 or in combination with growth hormone releasing factor and its analogs or growth hormone and its analogs. A still further use of the disclosed novel benzo-fused lactam growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis. A still further use of the disclosed novel benzo-fused lactam growth hormone secretagogues is in combination with IGF-1 to reverse the catabolic effects of nitrogen wasting as described by Kupfer, et al, *J. Clin. Invest.*, 91, 391 (1993).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids; treatment of osteoporosis; stimulation of the immune system; treatment of retardation; acceleration of wound healing; accelerating bone fracture repair; treatment of growth retardation, treating renal failure or insufficiency resulting in growth retardation; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS. Treatment of hyperinsulinemia including nesidioblastosis; adjuvant treatment for ovulation induction; to stimulate thymic development and prevent the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock and stimulation of wool growth in sheep.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/Kg of body weight daily are administered to patients and animals, e.g., mammals, to obtain effective release of growth hormone.

The following examples are provided for the purpose of further illustration only and are not intended to be limitations on the disclosed invention.

EXAMPLE 1

3-[(Furan-2-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide, trifluoroacetate To a stirred solution of 82 mg (0.14 mmol) of 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide hydrochloride dihydrate (prepared by the method of Fisher, et al, U.S. Pat. No. 5,206,235) in 4 mL of anhydrous methanol was added triethylamine (0.040 mL, 0.28 mmol) and then 3 Å powdered molecular sieves. To this was added dropwise a solution of furfuraldehyde (0.013 mL, 0.16 mmol). The pH was adjusted to the range pH 6-7 by the careful dropwise addition of a solution of 10% trifluoroacetic acid in methanol. The resulting mixture was stirred for 2 hours at ambient temperature and then 0.85 mL of a 1.0M solution of sodium cyanoborohydride in THF (0.85 mmol) was added dropwise. The mixture was stirred at room temperature overnight, quenched with 0.1 mL of trifluoroacetic acid, stirred for another hour, then filtered through Celite. The filtrate was concentrated under vacuum and purified by reverse phase HPLC on C18, eluting with methanol/0.1% aqueous trifluoroacetic acid using a linear gradient of 60% methanol to 75% methanol over ten minutes; retention time approximately 8.2 min. Concentration and lyophilization of the appropriate fractions gave the title compound (20.5 mg) as a white solid. $^1$H NMR (200 MHz, CD$_3$OD): $\delta$1.40 (s, 3H), 1.44 (s, 3H), 2.0-2.7 (m, 6H), 4.29 (s, 2H), 4.34 (dd; 8, 12 Hz; 1H), 4.89 (d, 15 Hz, 1H), 5.19 (d, 15 Hz, 1H), 6.41 (m, 1H), 6.56 (m, 1H), 6.96-7.06 (m, 3H), 7.1-7.4 (m, 7H), 7.45-7.70 (m, 4H). FAB-MS: calculated for $C_{34}H_{35}N_7O_3$ 589; found 590 (M+H, 100%).

EXAMPLE 2

3-[(Imidazol-2-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide; trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide hydrochloride dihydrate and 2-imidazolecarboxaldehyde by the procedure described in Example 1. Final purification carried was out by reverse phase HPLC on C18, eluting with methanol/0.1% aqueous trifluoroacetic acid using a linear gradient of 65% methanol to 80% methanol over ten minutes; retention time approximately 5.5 min. $^1$H NMR (200 MHz, CD$_3$OD): $\delta$1.41 (s, 3H), 1.45 (s, 3H), 2.0-2.7 (m, 6H), 4.37 (dd; 8, 12 Hz; 1H), 4.51 (s, 2H), 4.83 (d, 15 Hz, 1H), 5.23 (d, 15 Hz, 1H), 6.98 (d, 8 Hz, 2H), 7.1-7.4 (m, 7H), 7.4-7.7 (m, 5H). FAB-MS: calculated for $C_{33}H_{35}N_9O_2$ 589; found 590 (M+H, 83%).

EXAMPLE 3

3-[(5-Methylfuran-2-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide, trifluroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide hydrochloride dihydrate and 5-methylfuran-2-carboxaldehyde by the procedure described in Example 1. $^1$H NMR (200 MHz, CD$_3$OD): $\delta$1.41 (s, 3H), 1.44 (s, 3H), 2.00-2.76 (m, 6H), 2.25 (s, 3H), 4.24 (s, 2H), 4.38 (dd, 8, 12 Hz; 1H), 4.94 (d, 15 Hz, 1H), 5.22 (d, 15 Hz, 1H), 6.02 (d, 4 Hz, 1H), 6.45 (d, 4 Hz, 1H), 6.98 (d, 8 Hz, 2H), 7.16-7.42 (m, 7H), 7.46-7.76 (m, 5H). FAB-MS: calculated for $C_{35}H_{37}N_7O_3$ 603; found 604 (M+H, 85%).

EXAMPLE 4

3-[(Furan-2-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide, trifluoroacetate The title compound is prepared from 3-amino-3-methyl-N-[3,4-dihydro-4-oxo-5-[[2'-(1H-tetrazol-5-yl)[1,1'-biphenyl]-4-yl]-methyl]-1,5-benzothiazepin-3(S)-yl]butanamide, trifluoroacetate (prepared by the method of Fisher, et al, U.S. Pat. No. 5,206,235) and furfuraldehyde by the procedures described in Example 1.

EXAMPLE 5

N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide, trifluoroacetate Step A: 4-Methyl-2'-nitro-1,1'-biphenyl A vigorously stirred mixture of 4-tolylboronic acid (34 g, 0.25 mol) and 2-bromo-1-nitrobenzene (34 g, 0.168 mol) in a mixture of 5N sodium hydroxide (170 mL), water (57 mL), isopropanol (215 mL) and benzene (1080 mL) under a nitrogen atmosphere was treated with (tetrakis)triphenylphosphine palladium (0) (11.9 g). The stirred bilayer reaction mixture was heated at reflux for 3 hours. The cooled reaction mixture was filtered through Celite and the filter cake washed with fresh benzene. The organic layer was separated and washed with water (3×), dried over magnesium sulfate and filtered. The filtrate was evaporated under vacuum and the residue (46.1 g) purified by preparative high pressure liquid chromatography on silica gel, eluting with hexane/ethyl acetate (20:1) gave 28.05 g of the product. $^1$H NMR (400 MHz, CDCl$_3$): δ2.38 (s, 3H), 7.20 (m, 4H), 7.43 (m, 2H), 7.59 (t, 1H), 7.8 (d, 1H). EI-MS: calculated for C$_{13}$H$_{11}$NO$_2$ 213; found 213 (M+).

Step B: 4-Bromomethyl-2'-nitro-1,1'-biphenyl

A solution of 4-methyl-2'-nitro-1,1'-biphenyl (Step A) (6.0 g, 28.2 mmol), N-bromosuccinimide (4.99 g, 28.2 mmol). and AIBN (653 mg) in 75 mL of carbon tetrachloride was heated at reflux until a negative potassium iodide test was obtained (1.5 h). The reaction mixture was cooled and filtered. The filtrate was evaporated under vacuum to yield 8.41 g of crude product. $^1$H NMR revealed the product composition was approximatly 75% monobromo and 10% dibromo, in addition to 15% of unreacted starting material. $^1$H NMR. (200 MHz, CDCl$_3$): δ4.53 (s, 2H), 7.2–7.7 (m, 7H), 7.85 (m, 1H). EI-MS: calculated for C$_{14}$H$_{10}$BrN 272; found 272,274 (M+).

Step C: 4-Hydroxymethyl-2'-nitro-1,1'-biphenyl

A solution of 4-bromomethyl-2'-nitro-1,1'-biphenyl (7.27. g, 24.8 mmol) in acetic acid (50 mL) was treated with potassium acetate (4.88 g, 49.1 mmol). The reaction mixture was heated at reflux for 2 hours. After cooling, the reaction mixture was filtered and the precipitate was washed with acetic acid (2×). The filtrate was evaporated under vacuum and the residue was triturated with ethyl ether. The ether layer was washed consecutively with water, saturated aqueous sodium bicarbonate (3×) and water. The organic layer was dried over magnesium sulfate, filtered and evaporated under vacuum. The residue was dissolved in methanol (50 mL) and treated with a 6N methanolic potassium hydroxide solution (5 mL). After stirring for 1 hour at room temperature, thin layer chromatography indicated the absence of starting material. The reaction mixture was acidified with acetic acid and evaporated under vacuum. The residue was washed free of acetic acid by washing an etheral solution with aqueous sodium bicarbonate and water. After drying over magnesium sulfate, the ethereal solution was evaporated under vacuum. The residue was purified by preparative high pressure liquid chromatography on silica gel, eluting with hexane/ethyl acetate (3:1) to give 2'-nitro-1,1'-biphenyl-4-carboxaldehyde (620 mg) followed by 4-hydroxymethyl-2'-nitro-1,1'-biphenyl (3.06 g, 13.4 mmol, 54%).

Step D: 4-(Tetrahydropyranyloxy)methyl-2'-nitro-1,1'-biphenyl

A solution of 4-hydroxymethyl-2'-nitro-1,1'-biphenyl (3.06 g, 13.4 mmol) and 3,4-dihydropyran (1.8 mL, 20 mmol) in methylene chloride (50 mL) under a nitrogen atmosphere was treated with pyridinium p-toluenesulfonate (336 mg, 1.34 mmol). After stirring for 3 hours at room temperature, thin layer chromatography indicated that no starting material remained. The reaction mixture was diluted with ethyl ether (300 mL). The ether extracts were washed with saturated aqueous sodium chloride, dried over magnesium sulfate and filtered. The filtrate was evaporated under vacuum and the residue purified by preparative high pressure liquid chromatography on silica gel, eluting with hexane/ethyl acetate (10:1) to give 4.47 g of the product.

Step E: 4-(Tetrahydropyranyloxy)methyl-2'-amino-1,1'-biphenyl

A solution of 4-(tetrahydropyranyloxy)methyl-2'-nitro-1,1'-biphenyl (4.12 g, 13.2 mmol) in 100 mL of methanol was hydrogenated at 40 psi in the presence of 5% palladium on carbon. After 2 hours, uptake of hydrogen was complete. The reaction mixture was filtered through diatomacious earth, and the filter cake washed with methanol. The filtrate was evaporated under vacuum to yield 3.57 g of the product.

Step E: 4-Hydroxymethyl-2'-(methoxycarbonyl)amino-1,1'-biphenyl

A solution of (tetrahydropyranyloxy)methyl-2-amino-1,1'-biphenyl (500 mg, 1.76 mmol) in pyridine (6 mL) was treated with methyl chloroformate (0.41 mL, 5.3 mmol). The reaction mixture was stirred at room temperature for 48 hours. The reaction mixture was evaporated under vacuum. The residue was taken up in ethyl ether and washed with water (3×). The ether layer was dried over magnesium sulfate, filtered and evaporated under vacuum to yield 547 mg of crude 4-(tetrahydropyranyloxy)methyl-2'-(methoxycarbonyl)amino-1,1'-biphenyl.

The crude 4-(tetrahydropyranyloxy)methyl-2'-(methoxycarbonyl)amino-1,1'-biphenyl (250 mg) dissolved in 4 mL of methanol was treated with 1 mL of 10% methanolic p-toluenesulfonic acid. The reaction mixture was stirred at room temperature for 1 hour. The s reaction mixture was made basic by the addition of saturated aqueous sodium bicarbonate, then diluted with ethyl acetate. The organic layer was washed with water (2×), dried over magnesium sulfate and evaporated under vacuum. The residue was purified by preparative thin layer chromatography on silica gel, eluting with methylene chloride-methanol (100:3) to give 137 mg of the product. $^1$H NMR (200 MHz, CDCl$_3$): δ3.51 (s, 3H), 4.75 (s, 2H), 6.62 (br s, 1H), 7.14 (dd, 2H), 7.34 (dd, 1H), 7.4 (dd, 4H). FAB-MS (Li+ spike): calculated for C$_{15}$H$_{15}$NO$_3$ (257); found 264 (M+Li).

Step G: 4-Bromomethyl-2'-(methoxycarbonyl)amino-1,1'-biphenyl

A solution of 4-hydroxymethyl-2'-(methoxycarbonyl)amino-1,1'-biphenyl (239 mg, 0.93 mmol) in methylene chloride (4 mL) was treated with bromotrimethylsilane (3.0 mL, 22.7 mmol). The reaction mixture was stirred for 18 hours. The reaction mixture was diluted with additional methylene chloride and washed with saturated aqueous sodium chloride. After drying over magnesium sulfate, the filtered organic layer was evaporated under vacuum The residue was purified by preparative thin layer chromatography on silica gel, eluting with methylene chloride-methanol (100:3) to give 190 mg of the product.

Step H: N-[1-[[2'-[(Methoxycarbonyl)amino]][1,1'-biphenyl]-4-yl]methyl]-2,3,4,5-tetrahydro-2-oxo-1H-1-benzazepin-3(R)-yl -3-t-butoxycarbonylamino-3-methylbutanamide A solution of 222 mg (0.594 mmol) of 3-t-butoxycarbonylamino-3-methyl-N-[2,3,4,5-tetrahydro-2-oxo-1H-1-benzazepin-3(R)-yl]butanamide (prepared by the method of M. Fisher, et al, U.S. Pat. No. 5,206,235) in 6 mL of dry dimethylformamide was treated with 30 mg of 60% sodium hydride oil dispersion (18 mg NaH, 0.75 mmol, 1.3 eq). The reaction mixture was stirred at room temperature for 30 minutes. To the solution was added 190 mg (0.594 mmol) of solid 4-bromomethyl-2'-(methoxycarbonyl)amino-1,1'-biphenyl. After stirring at room temperature for 1 hour, the reaction mixture was diluted with ethyl acetate followed by 50 mL of water. The organic layer was washed with water (4×), dried over magnesium sulfate, filtered and evaporated under vacuum. The residue was purified by preparative thin layer chromatography on silica gel, eluting with methylene chloride/methanol (100:3) to give 231 mg (0.376 mmol, 63%) of the product. $^1$H NMR (400 MHz, CDCl$_3$): δ1.23 (s, 3H), 1.33 (s, 3H), 1.39 (s, 9H), 1.85 (m, 1H), 2.40 (dd, 2H), 2.49 (m, 1H), 2.54 (m, 2H), 3.68 (s, 3H), 4.53 (m, 1H), 4.94 (d, 1H), 5.17 (d, 1H), 6.53 (br s, 1H), 6.66 (d, 1H), 7.2 (m, 12H), 8.09 (d, 1H).

Step I: N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3-methylbutamide, trifluoroacetate A solution of 86 mg (0.14 mmol) of the intermediate obtained in Step H in 2 mL of methylene chloride was treated with 1.0 mL of trifluoroacetic acid. After stirring at room temperature for 1 hour, all volatiles were removed under vacuum and the residue purified by medium pressure liquid chromatography on C8, eluting with methanol/0.1% aqueous trifluoroacetic acid (60:40). The fractions containing the product were combined and solvents removed under vacuum. The residue was lyophilized from water to give 69 mg (0.13 mmol, 96%) of the product as a white solid. $^1$H NMR (400 MHz, CD$_3$OD): δ1.34 (s, 3H), 1.39 (s, 3H), 2.12 (m, 1H), 2.31 (m, 1H), 2.52 (dd, 2H), 2.6 (m, 2H), 3.54 (br s, 3H), 4.40 (dd, 1H), 5.02 (d, 1H), 5.28 (d, 1H), 7.30 (m, 12H), 7.54 (br s, 1H). FAB-MS: calculated for C$_{30}$H$_{34}$N$_4$O$_4$ 514; found 515 (M+H).

Step J: N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide, trifluoroacetate The title compound is prepared from N-[1-[[2'-[(methoxycarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Step I) and furfuraldehyde by the procedures described in Example 1.

EXAMPLE 6

N-[1-[[2'-[(Methylaminocarbonyl)amino][1,1'-biphenyl]-4-yl]methyl]2,3,4,5-tetrahydro-2-oxo-1H-1-benzazepin-3(R)-yl]-3-[(furan-2-yl)methyl]amino-3-methylbutanamide, trifluoroacetate Step A: N-[1-[[(2'-Nitro)[1,1'-biphenyl]-4-yl]methyl]-2,3,4,5-tetrahydro-2-oxo-1H-1-benzazepin-3(R)-yl]amino-3-methylbutanamide, trifluoroacetate Prepared from 4-bromomethyl-2'-nitro-1,1'-biphenyl (Example 5, Step B) and 3-t-butoxycarbonylamino-3-methyl-N-[2,3,4,5-tetrahydro-2-oxo-1H-1-benzazepin-3(R)-yl]butanamide (prepared by the method of M. Fisher, et al, U.S. Pat. No. 5,206,235) by the procedure described in Example 5, Step H. $^1$H NMR (400 MHz, CDCl$_3$): δ1.34 (s, 6H), 1.41 (s, 9H), 1.83 (m, 1H), 2.35–2.70 (m, 5H), 4.50 (m, 1H), 4.84 (d, 15 Hz, 1H), 5.23 (d, 15 Hz, 1H), 5.27 (s, 1H), 6.64 (d, 7 Hz, 1H), 7.1–7.6 (m, 11H), 7.80 (d, 8 Hz, 1H). FAB-MS: calculated for C$_{33}$H$_{38}$N$_4$O$_6$ 586; found 587 (M+H).

Step B: N-[1-[[(2'-Amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 7.79 g (13.23 mmol) of the intermediate obtained in Step A in 200 mL of methanol containing 0.9 g of 5% palladium on carbon was hydrogenated at 40 psi. When the uptake of hydrogen was complete, the catalyst was removed by filtration through Celite. The filtrate was concentrated under vacuum to yield 6.6 g (11.9 mmol, 90%) of product. $^1$H NMR (400 MHz, CDCl$_3$): δ1.32 (s, 6H), 1.39 (s, 9H), 1.87 (m, 1H), 2.51 (dd, 1H), 2.59 (m, 1H), 4.51 (m, 1H), 4.89 (d, 1H), 5.15 (d, 1H), 5.32 (br s, 1H), 6.71 (d, 1H), 6.81 (s, 1H), 7.21 (m, 10H). FAB-MS: calculated for C$_{33}$H$_4$N$_4$O$_4$ 556; found 557 (M+H).

Step C: N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 88.4 mg (0.158 mmol) of the intermediate obtained in Step B in 4 mL of methylene chloride at room temperature was treated with 0.5 mL of methyl isocyanate (8.5 mmol). The reaction mixture was stirred at room temperature for 18 hours, when all starting material was consumed as indicated by thin layer chromatography. The reaction was evaporated under vacuum and the residue passed over silica gel. Elution with ethyl acetate/n-hexane (3:1) yielded 66 mg (0.11 mmol, 68%) of product. $^1$H NMR (400 MHz, CDCl$_3$): δ1.21 (s, 3H), 1.23 (s, 3H), 1.39 (s, 9H), 1.89 (m, 1H), 2.49 (dd, H), 2.60 (m, 2H), 2.69 (s, 3H), 4.50 (m, 1H), 4.95 (d, 1H), 5.06 (d, 1H), 5.26 (br s, 1H), 6.24 (br s, 1H), 6.70 (d, 1H), 7.22 (m, 11H), 7.71 (d, 1H).

Step D: N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 66 mg (0.11 mmol) of the intermediate obtained in Step C in 2 mL of methylene chloride was treated with 2 mL of trifluoroacetic acid. The reaction mixture was stirred at room temperature for 1 hour, when thin layer chromatography indicated that no starting material remained. The reaction mixture was evaporated to dryness under vacuum and the residue purified by medium pressure liquid chromatography on C8, eluting with methanol/0.1% aqueous trifluoroacetic acid (60:40). Fractions containing the product were combined and evaporated under vacuum and the residue lyophilized from water to give 26 mg (0.051 mmol, 46%) of the product as a white solid. $^1$H NMR (400 MHz, CD$_3$OD): δ1.34 (s, 3H), 1.37 (s, 3H), 2.13 (m, 1H), 2.39 (m, 1H), 2.54 (dd, 1H), 2.63 (s, 3H), 3.29 (dd, 1H), 4.95 (d, 1H), 5.11 (d, 1H), 7.22 (m, 10H), 7.60 (d, 1H). FAB-MS: calculated for C$_{30}$H$_{35}$N$_5$O$_3$ 513; found 536 (M+Na).

Step E: N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide, trifluoroacetate The title compound is prepared from N-[1-[[2'-[(methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide trifluoroacetate (Step D) and furfuraldehyde by the procedures described in Example 1.

EXAMPLE 7

3-[(Furan-2-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide The title compound is prepared from 3-amino-3-methyl-N-[3,4-dihydro-4-oxo-5-[[2'-(1H-tetrazol-5-yl)[1,1'-biphenyl]-4-yl]methyl]-1,5-benzothiazepin-3(S)-yl]butanamide trifluoroacetate (prepared by the method of M. Fisher, et al, U.S. Pat. No. 5,206,235) and furfuraldehyde by the procedures described in Example 1.

EXAMPLE 8

Utilizing the procedures described in Examples 1 to 7 and general methods of organic synthesis described in the chemical literature and familiar to one skilled in the art, the following compounds of Formula 1 can be prepared from the appropriately substituted starting materials and reagents.

| $R^1$ | $R^9$ | A | $R^4$ |
|---|---|---|---|
| 6-F | —NH—C(=O)—NHCH$_3$ | —CH$_2$—C(CH$_3$)(CH$_3$)— | —CH$_2$-furan |
| 7-F | —NH—C(=O)—NHCH$_3$ | —CH$_2$—C(CH$_3$)(CH$_3$)— | —CH$_2$-furan |
| 7-CF$_3$ | —NH—C(=O)—NHCH$_3$ | —CH$_2$—C(CH$_3$)(CH$_3$)— | —CH$_2$-furan |
| 7-OCH$_3$ | —NH—C(=O)—NHCH$_3$ | —CH$_2$—C(CH$_3$)(CH$_3$)— | —CH$_2$-furan |
| 7-OH | —NH—C(=O)—NHCH$_3$ | —CH$_2$—C(CH$_3$)(CH$_3$)— | —CH$_2$-furan |
| H | tetrazole | —C(CH$_3$)(CH$_3$)— | —CH$_2$-furan |
| H | tetrazole | —C(H)(CH$_3$)— | —CH$_2$-furan |
| H | tetrazole | —C(CH$_3$)(H)— | —CH$_2$-furan |

-continued

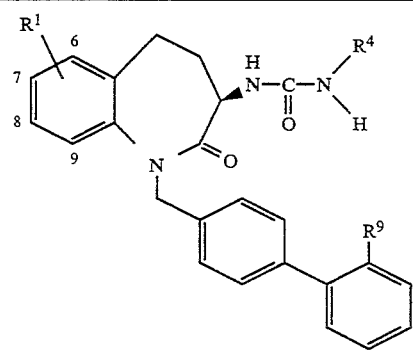

| R¹ | R⁹ | A | R⁴ |
|---|---|---|---|
| H | 5-tetrazolyl (NH) | -C(H)(CH₂OH)- | -CH₂-(2-furyl) |
| H | 5-tetrazolyl (NH) | -C(CH₃)(CH₂OH)- | -CH₂-(2-furyl) |
| H | -C(O)-NHCH₃ | -C(H)(CH₃)- | -CH₂-(2-furyl) |
| H | -C(O)-NHCH₃ | -CH₂-C(CH₃)(CH₂OH)- | -CH₂-(2-furyl) |
| H | -C(O)-NHCH₃ | -CH₂-C(CH₃)(CH₂OH)- (HOCH₂ up) | -CH₂-(2-furyl) |
| H | -C(O)-NHCH₃ | -CH₂-C(CH₃)(CH₂OH)- (HOCH₂ up) | -CH₂-(2-furyl) |
| H | -C(O)-NHCH₃ | -CH₂-C(CH₃)(CH₂OH)- (HOCH₂ up) | -CH₂-(2-furyl) |
| H | 5-tetrazolyl (NH) | -C(CH₃)(CH₃)- | -CH₂-(oxazolyl) |
| H | 5-tetrazolyl (NH) | -CH₂-C(CH₃)(CH₃)- | -CH₂-(oxazolyl) |
| H | 5-tetrazolyl (NH) | -C(CH₃)(CH₃)- | -CH₂-(benzofuryl) |

-continued

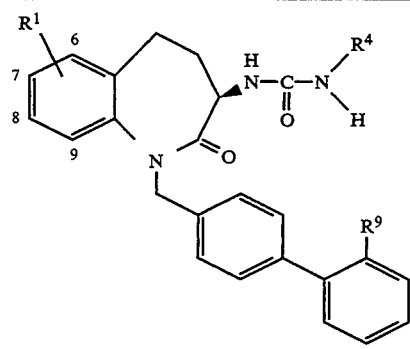

| R¹ | R⁹ | A | R⁴ |
|---|---|---|---|
| H | tetrazole (NH) | —CH₂—C(CH₃)(CH₃)— | —CH₂-benzofuran |
| H | —C(O)—NHCH₃ | —C(CH₃)(CH₃)— | —CH₂-oxazole |
| H | —C(O)—NHCH₃ | —CH₂—C(CH₃)(CH₃)— | —CH₂-oxazole |
| H | —C(O)—NHCH₃ | —C(CH₃)(CH₃)— | —CH₂-benzofuran |
| H | —C(O)—NHCH₃ | —CH₂—C(CH₃)(CH₃)— | —CH₂-benzofuran |
| H | —NH—C(O)—NHCH₃ | —C(CH₃)(CH₃)— | —CH₂-oxazole |
| H | —NH—C(O)—NHCH₃ | —CH₂—C(CH₃)(CH₃)— | —CH₂-oxazole |
| H | —NH—C(O)—NHCH₃ | —C(CH₃)(CH₃)— | —CH₂-benzofuran |
| H | —NH—C(O)—NHCH₃ | —CH₂—C(CH₃)(CH₃)— | —CH₂-benzofuran |
| H | —CH₂NH—C(O)—NHCH₃ | —C(CH₃)(CH₃)— | —CH₂-oxazole |

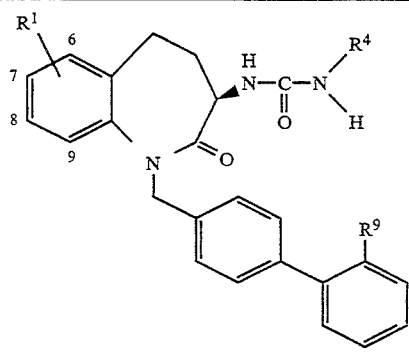

| R¹ | R⁹ | A | R⁴ |
|---|---|---|---|
| H | −CH₂NH−C(O)−NHCH₃ | −CH₂−C(CH₃)(CH₃)− | −CH₂−(oxazole) |
| H | −CH₂NH−C(O)−NHCH₃ | −C(CH₃)(CH₃)− | −CH₂−(benzofuran) |
| H | −CH₂NH−C(O)−NHCH₃ | −CH₂−C(CH₃)(CH₃)− | −CH₂−(benzofuran) |

EXAMPLE 9

Utilizing the procedures described in Examples 1 to 7 and general methods of organic synthesis described in the chemical literature and familiar to one skilled in the art, the following compounds of Formula I can be prepared from the appropriately substituted starting materials and reagents.

| X | n | p | R⁹ | A | R⁴ |
|---|---|---|---|---|---|
| — | 0 | 3 | −NH−C(O)−NHCH₃ | −CH₂−C(CH₃)(CH₃)− | −CH₂−(furan) |
| — | 0 | 3 | −C(O)−NHCH₂CH₃ | −CH₂−C(CH₃)(CH₃)− | −CH₂−(furan) |
| — | 0 | 1 | −NH−C(O)−NHCH₃ | −CH₂−C(CH₃)(CH₃)− | −CH₂−(furan) |

-continued

![structure with (X)n-(CH2)p, phenyl, NHC(O)A-NHR4, biphenyl with R9]

| X | n | p | R⁹ | A | R⁴ |
|---|---|---|---|---|---|
| — | 0 | 1 | -C(O)-NHCH₂CH₃ | -CH₂-C(CH₃)(CH₃)- | -CH₂-furan |
| — | 0 | 0 | -NH-C(O)-NHCH₃ | -CH₂-C(CH₃)(CH₃)- | -CH₂-furan |
| — | 0 | 0 | -C(O)-NHCH₂CH₃ | -CH₂-C(CH₃)(CH₃)- | -CH₂-furan |
| C=O | 1 | 1 | -NH-C(O)-NHCH₃ | -CH₂-C(CH₃)(CH₃)- | -CH₂-furan |
| CHOH | 1 | 1 | -NH-C(O)-NHCH₃ | -CH₂-C(CH₃)(CH₃)- | -CH₂-furan |
| S | 1 | 0 | -NH-C(O)-NHCH₃ | -CH₂-C(CH₃)(CH₃)- | -CH₂-furan |
| S | 1 | 0 | -C(O)-NH₂ | -CH₂-C(CH₃)(CH₃)- | -CH₂-furan |
| S | 1 | 0 | tetrazole | -CH₂-C(CH₃)(CH₃)- | -CH₂-furan |
| SO | 1 | 0 | -NH-C(O)-NHCH₃ | -CH₂-C(CH₃)(CH₃)- | -CH₂-furan |
| SO | 1 | 0 | tetrazole | -CH₂-C(CH₃)(CH₃)- | -CH₂-furan |
| SO | 1 | 0 | -C(O)-NHCH₃ | -CH₂-C(CH₃)(CH₃)- | -CH₂-furan |
| SO | 1 | 0 | -NH-C(O)-NH₂ | -CH₂-C(CH₃)(CH₃)- | -CH₂-furan |

-continued

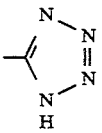

| X | n | p | R⁹ | A | R⁴ |
|---|---|---|---|---|---|
| S | 1 | 2 | −NH−C(=O)−NHCH₃ | −CH₂−C(CH₃)(CH₃)− | −CH₂-furan |
| S | 1 | 2 | tetrazole-NH | −CH₂−C(CH₃)(CH₃)− | −CH₂-furan |
| S | 1 | 2 | −C(=O)−NHCH₃ | −CH₂−C(CH₃)(CH₃)− | −CH₂-furan |
| S | 1 | 2 | −CH₂OH | −CH₂−C(CH₃)(CH₃)− | −CH₂-furan |
| S | 1 | 2 | −NH−C(=O)−NHCH₃ | −CH₂−C(CH₃)(CH₃)− | −CH₂-furan |
| S | 1 | 2 | −C(=O)−NHCH₃ | −CH₂−C(CH₃)(CH₃)− | −CH₂-furan |
| S | 1 | 2 | tetrazole-NH | −CH₂−C(CH₃)(CH₃)− | −CH₂-furan |
| S | 1 | 2 | −CH₂OH | −CH₂−C(CH₃)(CH₃)− | −CH₂-furan |
| O | 1 | 1 | −NH−C(=O)−NHCH₃ | −CH₂−C(CH₃)(CH₃)− | −CH₂-furan |
| O | 1 | 1 | −C(=O)−NHCH₃ | −CH₂−C(CH₃)(CH₃)− | −CH₂-furan |
| O | 1 | 1 | tetrazole-NH | −CH₂−C(CH₃)(CH₃)− | −CH₂-furan |

-continued

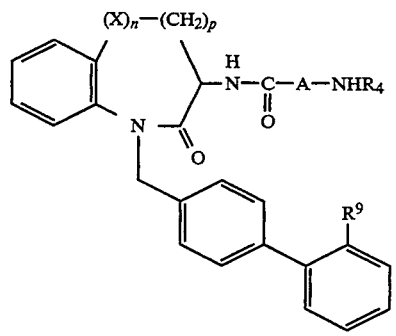

| X | n | p | R⁹ | A | R⁴ |
|---|---|---|---|---|---|
| O | 1 | 1 | —CH₂OH | —CH₂—C(CH₃)(CH₃)— | —CH₂-furan |

EXAMPLE 10

Utilizing the procedures described in Examples 1 to 7 and general methods of organic synthesis described in the chemical literature and familiar to one skilled in the art, the following compounds of Formula 1 can be prepared from the appropriately substituted starting materials and reagents.

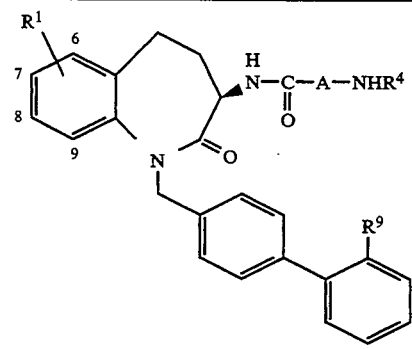

| R¹ | R⁹ | A | R⁴ |
|---|---|---|---|
| H | —CH₂NH—C(=O)—NH₂ | —CH₂—C(CH₃)(CH₃)— | —CH₂-furan |
| 7-F | —CH₂NH—C(=O)—NH₂ | —CH₂—C(CH₃)(CH₃)— | —CH₂-furan |
| 8-F | —CH₂NH—C(=O)—NH₂ | —CH₂—C(CH₃)(CH₃)— | —CH₂-furan |
| 7-CF₃ | —CH₂NH—C(=O)—NH₂ | —CH₂—C(CH₃)(CH₃)— | —CH₂-furan |
| 7-CH₃S | —CH₂NH—C(=O)—NH₂ | —CH₂—C(CH₃)(CH₃)— | —CH₂-furan |
| 7-CH₃O | —CH₂NH—C(=O)—NH₂ | —CH₂—C(CH₃)(CH₃)— | —CH₂-furan |

-continued

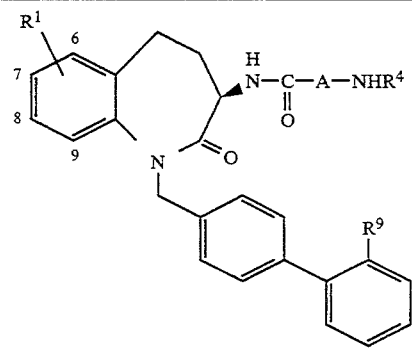

| R[1] | R[9] | A | R[4] |
|---|---|---|---|
| 8-F | —CH₂NH—C(=O)—NHCH₃ | —CH₂—C(CH₃)(CH₃)— | —CH₂-(2-furyl) |
| 7-CF₃ | —CH₂NH—C(=O)—NHCH₃ | —CH₂—C(CH₃)(CH₃)— | —CH₂-(2-furyl) |
| H | —CH₂NH—C(=O)—NHCH₃ | —CH₂—C(CH₃)(CH₂OH)— | —CH₂-(2-furyl) |
| 7-F | —CH₂NH—C(=O)—NHCH₃ | —CH₂—C(CH₃)(CH₂OH)— | —CH₂-(2-furyl) |
| 7-F | —CH₂NH—C(=O)—NHCH₃ | —CH₂—C(HOCH₂)(CH₃)— | —CH₂-(2-furyl) |
| 6-F | —CH₂NH—C(=O)—NH₂ | —CH₂—C(CH₃)(CH₃)— | —CH₂-(2-furyl) |
| 6-OCH₃ | —CH₂NH—C(=O)—NH₂ | —CH₂—C(CH₃)(CH₃)— | —CH₂-(2-furyl) |
| 7-Br | —CH₂NH—C(=O)—NH₂ | —CH₂—C(CH₃)(CH₃)— | —CH₂-(2-furyl) |
| 7-Cl | —CH₂NH—C(=O)—NH₂ | —CH₂—C(CH₃)(CH₃)— | —CH₂-(2-furyl) |
| 7-CH₃ | —CH₂NH—C(=O)—NH₂ | —CH₂—C(CH₃)(CH₃)— | —CH₂-(2-furyl) |
| 8-Cl | —CH₂NH—C(=O)—NH₂ | —CH₂—C(CH₃)(CH₃)— | —CH₂-(2-furyl) |
| 8-I | —CH₂NH—C(=O)—NH₂ | —CH₂—C(CH₃)(CH₃)— | —CH₂-(2-furyl) |
| H | —CH₂NH—C(=O)—N(CH₃)₂ | —CH₂—C(CH₃)(CH₃)— | —CH₂-(2-furyl) |

-continued

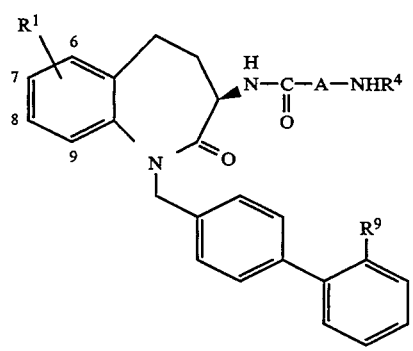

| R¹ | R⁹ | A | R⁴ |
|---|---|---|---|
| H | —CH₂NH—C(=O)—NHCH(CH₃)₂ | —CH₂—C(CH₃)₂— | —CH₂-(furan) |
| H | —CH₂N(CH₃)—C(=O)—NHCH₃ | —CH₂—C(CH₃)₂— | —CH₂-(furan) |
| H | —CH₂NH—C(=O)—NHCH₂Ph | —CH₂—C(CH₃)₂— | —CH₂-(furan) |
| H | —CH₂NH—C(=O)—N(pyrrolidine) | —CH₂—C(CH₃)₂— | —CH₂-(furan) |
| H | —CH₂NH—C(=O)—N(morpholine) | —CH₂—C(CH₃)₂— | —CH₂-(furan) |
| H | —CH₂NH—C(=O)—N(piperazine-NH) | —CH₂—C(CH₃)₂— | —CH₂-(furan) |

EXAMPLE 11

Utilizing the procedures described in Examples 1 to 7 and general methods of organic synthesis described in the chemical literature and familiar to one skilled in the art, the following compounds of Formula I can be prepared from the appropriately substituted starting materials and reagents.

| X | n | p | R⁹ | A | R⁴ |
|---|---|---|---|---|---|
| — | 0 | 3 | —CH₂NH—C(=O)—NH₂ | —CH₂—C(CH₃)(CH₃)— | —CH₂-furyl |
| — | 0 | 3 | —CH₂NH—C(=O)—NHCH₃ | —CH₂—C(CH₃)(CH₃)— | —CH₂-furyl |
| — | 0 | 3 | —CH₂NH—C(=O)—OCH₃ | —CH₂—C(CH₃)(CH₃)— | —CH₂-furyl |
| — | 0 | 1 | —CH₂NH—C(=O)—NHCH₃ | —CH₂—C(CH₃)(CH₃)— | —CH₂-furyl |
| — | 0 | 1 | —CH₂NH—C(=O)—OCH₃ | —CH₂—C(CH₃)(CH₃)— | —CH₂-furyl |
| — | 0 | 1 | —CH₂NH—C(=O)—NH₂ | —CH₂—C(CH₃)(CH₃)— | —CH₂-furyl |
| — | 0 | 0 | —CH₂NH—C(=O)—NH₂ | —CH₂—C(CH₃)(CH₃)— | —CH₂-furyl |
| — | 0 | 0 | —CH₂NH—C(=O)—NHCH₃ | —CH₂—C(CH₃)(CH₃)— | —CH₂-furyl |
| — | 0 | 0 | —CH₂NH—C(=O)—OCH₃ | —CH₂—C(CH₃)(CH₃)— | —CH₂-furyl |
| C=O | 1 | 1 | —CH₂NH—C(=O)—NHCH₃ | —CH₂—C(CH₃)(CH₃)— | —CH₂-furyl |
| CHOH | 1 | 1 | —CH₂NH—C(=O)—NHCH₃ | —CH₂—C(CH₃)(CH₃)— | —CH₂-furyl |
| S | 1 | 0 | —CH₂NH—C(=O)—NHC₂H₅ | —CH₂—C(CH₃)(CH₃)— | —CH₂-furyl |
| S | 1 | 0 | —CH₂NH—C(=O)—NH₂ | —CH₂—C(CH₃)(CH₃)— | —CH₂-furyl |

-continued

| X | n | p | R⁹ | A | R⁴ |
|---|---|---|---|---|---|
| S | 1 | 0 | —CH₂NH—C(=O)—OCH₃ | —CH₂—C(CH₃)(CH₃)— | —CH₂-(furan) |
| SO | 1 | 0 | —CH₂NH—C(=O)—NHCH₃ | —CH₂—C(CH₃)(CH₃)— | —CH₂-(furan) |
| SO | 1 | 0 | —CH₂NH—C(=O)—NH₂ | —CH₂—C(CH₃)(CH₃)— | —CH₂-(furan) |
| SO | 1 | 0 | —CH₂NH—C(=O)—N(CH₃)₂ | —CH₂—C(CH₃)(CH₃)— | —CH₂-(furan) |
| SO | 1 | 0 | —CH₂NH—C(=O)—OCH₃ | —CH₂—C(CH₃)(CH₃)— | —CH₂-(furan) |
| S | 1 | 2 | —CH₂NH—C(=O)—NH₂ | —CH₂—C(CH₃)(CH₃)— | —CH₂-(furan) |
| S | 1 | 2 | —CH₂NH—C(=O)—NHCH₃ | —CH₂—C(CH₃)(CH₃)— | —CH₂-(furan) |
| S | 1 | 2 | —C(=O)—NH₂ | —CH₂—C(CH₃)(CH₃)— | —CH₂-(furan) |
| S | 1 | 2 | —C(=O)—NHCH₃ | —CH₂—C(CH₃)(CH₃)— | —CH₂-(furan) |
| S | 1 | 2 | —C(=O)—morpholino | —CH₂—C(CH₃)(CH₃)— | —CH₂-(furan) |
| S | 1 | 2 | tetrazolyl (NH) | —CH₂—C(CH₃)(CH₃)— | —CH₂-(furan) |
| S | 1 | 2 | —CH₂OH | —CH₂—C(CH₃)(CH₃)— | —CH₂-(furan) |

| X | n | p | R⁹ | A | R⁴ |
|---|---|---|---|---|---|
| S | 1 | 2 | —CH₂C(O)—NHCH₃ | —CH₂—C(CH₃)(CH₃)— | —CH₂-furyl |
| O | 1 | 1 | —C(O)—NH₂ | —CH₂—C(CH₃)(CH₃)— | —CH₂-furyl |
| O | 1 | 1 | —C(O)—NHCH₃ | —CH₂—C(CH₃)(CH₃)— | —CH₂-furyl |
| O | 1 | 1 | —C(O)—N-morpholino | —CH₂—C(CH₃)(CH₃)— | —CH₂-furyl |
| O | 1 | 1 | tetrazolyl | —CH₂—C(CH₃)(CH₃)— | —CH₂-furyl |

What is claimed is:

1. A compound having the formula:

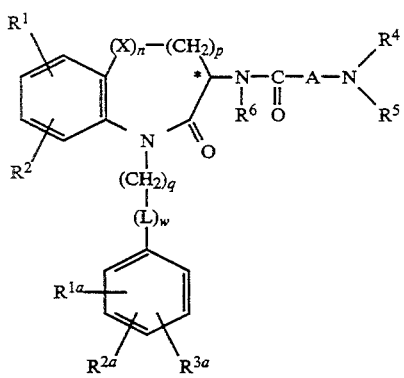

I where
L is

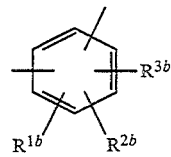

n is 0 or 1;
p is 0 to 3;
q is 0 to 4;
w is 0 or 1;
X is C=O, O, S(O)$_m$, $$-\underset{|}{\overset{OH}{CH}}-, \quad -\underset{|}{\overset{R^{10}}{N}}- \quad \text{or} \quad -CH=CH-;$$

m is 0 to 2;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, R$^{7b}$O(CH₂)$_v$—, R$^{7b}$COO(CH₂)$_v$—, R$^{7b}$OCO(CH₂)$_v$—, R$^{5b}$R$^{12b}$N(CH₂)$_v$—, R$^{7b}$CON(R$^{12b}$)(CH₂)$_v$—, R$^{5b}$R$^{12b}$NCO(CH₂)$_v$—, phenyl or substituted phenyl where the substituents are from 1 to 3 of halogen, $C_1$-$C_6$ alkyl, $C_1$-$C_6$ alkoxy, or hydroxy; and v is 0 to 3;

$R^{7a}$ and $R^{7b}$ are independently hydrogen, $C_1$-$C_3$ perfluoroalkyl, $C_1$-$C_6$ alkyl, substituted $C_1$-$C_6$ alkyl where the substitutents are phenyl or substituted phenyl; phenyl or substituted phenyl where the phenyl substitutents are from 1 to 3 of halogen, $C_1$-$C_6$ alkyl, $C_1$-$C_6$ alkoxy or hydroxy;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is

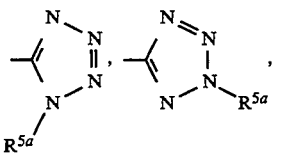

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^{5b}R^{12b}N(CH_2)_v$—, $R^{5b}R^{12b}NCO(CH_2)_v$—, $R^{5b}R^{12b}NCS(CH_2)_v$—, $R^{5b}R^{12c}NN(R^{12b})CO(CH_2)_v$—, $R^{5b}R^{12a}NN(R^{12b})CS(CH_2)_v$—, $R^{5b}R^{12b}NCON(R^{12a})(CH_2)_v$—, $R^{5b}R^{12b}NCSN(R^{12a})(CH_2)_v$—, $R^{5b}R^{12c}NN(R^{12b})CSN(R^{12a})(CH_2)_v$—, $R^{5b}R^{12c}NN(R^{12b})CON(R^{12a})(CH_2)_v$—, $R^{5b}R^{12c}(R^{12b})COO(CH_2)_v$—, $R^{5b}R^{12b}NCOO(CH_2)_v$— or $R^{13}OCON(R^{12a})(CH_2)_v$—, where v is 0 to 3;

$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substitutents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^{10}$ and $R^{11}$ are independently hydrogen, $C_1$-$C_6$ alkyl, phenyl, phenyl $C_1$-$C_6$ alkyl, $C_1$-$C_5$ alkoxycarbonyl or $C_1$-$C_5$ alkanoyl-$C_1$-$C_6$ alkyl;

$R^5$, $R^{5a}$ and $R^{5b}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl or substituted $C_3$-$C_{10}$ alkynyl where the substitutents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_{20}$ alkanoyloxy, $C_1$-$C_5$ alkoxycarbonyl, carboxy, formyl or —$NR^{10}R^{11}$ where $R^1$, $R^2$, $R^{10}$ and $R^{11}$ are as defined above;

$R^4$ is $R^{14}$ or $C_1$-$C_{10}$ alkyl substituted with $R^{14}$;
$R^{14}$ is

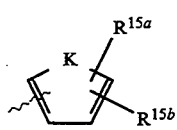

-continued

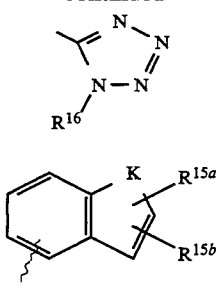

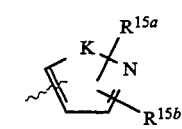

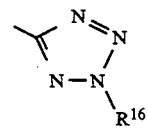

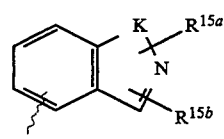

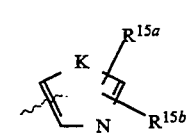

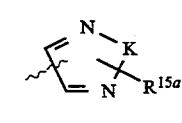

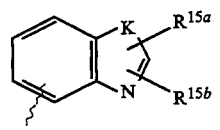

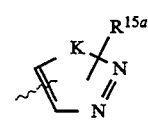

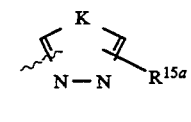

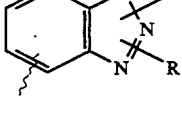

or

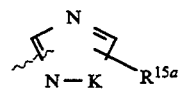

where
K is O, S or $NR^{16}$;

$R^{15a}$ and $R^{15b}$ are independently hydrogen, hydroxy, halogen, oxo, cyano, nitro, —S(O)$_m$R$^{7a}$, C$_1$–C$_3$ perfluoroalkyl, C$_1$–C$_3$ perfluoroalkoxy, R$^{12a}$R$^{12c}$N(CH$_2$)$_v$—, R$^{12a}$R$^{12b}$NCO(CH$_2$)$_v$—, C$_1$–C$_6$ alkoxy, phenyl, substituted phenyl, C$_1$–C$_{10}$ alkyl or substituted C$_1$–C$_{10}$ alkyl where the substituents on the phenyl or alkyl are from 1 to 5 of hydroxy, C$_1$–C$_6$ alkoxy, C$_3$–C$_7$ cycloalkyl, fluoro, R$^1$, R$^2$ independently disubstituted phenyl, R$^1$, R$^2$ independently disubstituted phenyl C$_1$–C$_3$ alkoxy, C$_1$–C$_6$ alkanoyloxy, C$_1$–C$_5$ alkoxycarbonyl, carboxy, formyl or —NR$^{10}$R$^{11}$ where R$^1$, R$^2$, R$^{7a}$, R$^{10}$, R$^{11}$, R$^{12a}$, R$^{12b}$, R$^{12c}$, m and v are as defined above;

R$^{16}$ is hydrogen, C$_1$–C$_6$ alkyl or substituted C$_1$–C$_6$ alkyl where the substituents are from 1 to 3 of hydroxy, C$_1$–C$_6$ alkoxy, fluoro, R$^1$, R$^2$ independently disubstituted phenyl, R$^1$, R$^2$ independently disubstituted phenyl C$_1$–C$_3$ alkoxy, C$_1$–C$_6$ alkanoyloxy, C$_1$–C$_5$ alkoxycarbonyl, carboxy, C$_1$–C$_5$ alkanoyl-C$_1$–C$_6$ alkyl or —NR$^{10}$R$^{11}$ where R$^1$, R$^2$, R$^{10}$ and R$^{11}$ are as defined above;

R$^6$ is hydrogen, C$_1$–C$_{10}$ alkyl, phenyl or phenyl C$_1$–C$_{10}$ alkyl;

A is

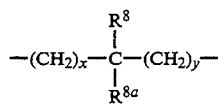

where x and y are independently 0–3;

R$^8$ and R$^{8a}$ are independently hydrogen, C$_1$–C$_{10}$ alkyl, trifluoromethyl, phenyl, substituted C$_1$–C$_{10}$ alkyl where the substituents are from 1 to 3 of imidazolyl, indolyl, hydroxy, fluoro, —S(O)$_m$R$^{7a}$, C$_1$–C$_6$ alkoxy, C$_3$–C$_7$ cycloalkyl, R$^1$, R$^2$ independently disubstituted phenyl, R$^1$, R$^2$ independently disubstituted phenyl C$_1$–C$_3$ alkoxy, C$_1$–C$_5$ alkanoyloxy, C$_1$–C$_5$ alkoxycarbonyl, carboxy, formyl or —NR$^{10}$R$^{11}$ where R$^1$, R$^2$, R$^{7a}$, R$^{10}$, R$^{11}$ and m are as defined above; or R$^8$ and R$^{8a}$ can be taken together to form —(CH$_2$)$_t$— where t is 2 to 6; and R$^8$ and R$^{8a}$ can independently be joined to R$^5$ to form alkylene bridges between the terminal nitrogen and the alkyl portion of the A group wherein the bridge contains from one to five carbon atoms; and pharmaceutically acceptable salts thereof.

2. A compound of claim 1 wherein:
n is 0 or 1;
p is 0 to 3;
q is 0 to 2;
w is 0 or 1;
X is O, S(O)$_m$,

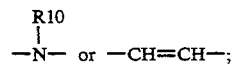

m is 0 to 2;

R$^1$, R$^2$, R$^{1a}$, R$^{2a}$, R$^{1b}$ and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$–C$_6$ alkyl, C$_1$–C$_6$ alkoxy, or hydroxy;

R$^{7a}$ and R$^{7b}$ are independently hydrogen, C$_1$–C$_3$ perfluoroalkyl, C$_1$–C$_6$ alkyl, substituted C$_1$–C$_6$ alkyl where the substituents are phenyl; phenyl and v is 0 to 3;

R$^{3a}$ and R$^{3b}$ are independently hydrogen, R$^9$, C$_1$–C$_6$ alkyl substituted with R$^9$, phenyl substituted with R$^9$ or phenoxy substituted with R$^9$;

R$^9$ is

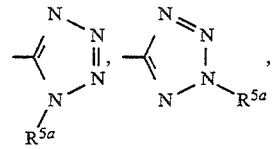

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{5b}$R$^{12b}$N(CH$_2$)$_v$—, R$^{5b}$R$^{12b}$NCO(CH$_2$)$_v$—, R$^{5b}$R$^{12b}$NCS(CH$_2$)$_v$—, R$^{5b}$R$^{12c}$NN(R$^{12b}$)CO(CH$_2$)$_v$—, R$^{5b}$R$^{12b}$NCON(R$^{12a}$)(CH$_2$)$_v$—, R$^{5b}$R$^{12b}$NCSN(R$^{12a}$)(CH$_2$)$_v$—, R$^{5b}$R$^{12c}$NN(R$^{12b}$)CSN(R$^{12a}$)(CH$_2$)$_v$—, R$^{5b}$R$^{12c}$NN(R$^{12b}$)CON(R$^{12a}$)(CH$_2$)$_v$—, R$^{5b}$R$^{12c}$NN(R$^{12b}$)COO(CH$_2$)$_v$—, R$^{5b}$R$^{12b}$NCOO(CH$_2$)$_v$— or R$^{13}$OCON(R$^{12a}$)(CH$_2$)$_v$—, where v is 0 to 3;

R$^{12a}$, R$^{12b}$ and R$^{12c}$ are independently R$^{5a}$, OR$^{5a}$ or COR$^{5a}$; R$^{12a}$ and R$^{12b}$, or R$^{12b}$ and R$^{12c}$, or R$^{12a}$ and R$^{12c}$, or R$^{12b}$ and R$^{5b}$, or R$^{12c}$ and R$^{5b}$, or R$^{13}$ and R$^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and R$^1$ and R$^{10}$ are as defined;

R$^{13}$ is C$_1$–C$_3$ perfluoroalkyl, C$_1$–C$_6$ alkyl, substituted C$_1$–C$_6$ alkyl, where the substituents are hydroxy, —NR$^{10}$R$^{11}$, carboxy, phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;

R$^{10}$ and R$^{11}$ are independently hydrogen, C$_1$–C$_6$ alkyl, phenyl C$_1$–C$_6$ alkyl, or C$_1$–C$_5$ alkanoyl-C$_1$–C$_6$ alkyl;

R$^5$, R$^{5a}$ and R$^{5b}$ are independently hydrogen, phenyl, substituted phenyl, C$_1$–C$_{10}$ alkyl or substituted C$_1$–C$_{10}$ alkyl where the substituents on the phenyl or alkyl are from 1 to 5 of hydroxy, C$_1$–C$_6$ alkoxy, C$_3$–C$_7$ cycloalkyl, fluoro, R$^1$, R$^2$ independently disubstituted phenyl, R$^1$, R$^2$ independently disubstituted phenyl C$_1$–C$_3$ alkoxy, C$_1$–C$_{20}$ alkanoyloxy, C$_1$–C$_5$ alkoxycarbonyl, carboxy or formyl where R$^1$ and R$^2$ are as defined above;

R$^4$ is R$^{14}$ or C$_1$–C$_6$ alkyl substituted with R$^{14}$;
R$^{14}$ is as defined above;
R$^{15a}$ and R$^{15b}$ are independently hydrogen, hydroxy, halogen, —S(O)$_m$R$^{7a}$, C$_1$–C$_3$ perfluoroalkyl, R$^{12a}$R$^{12c}$N(CH$_2$)$_v$—, R$^{12a}$R$^{12b}$NCO(CH$_2$)$_v$—, C$_1$–C$_6$ alkoxy, phenyl, substituted phenyl, C$_1$–C$_{10}$ alkyl or substituted C$_1$–C$_{10}$ alkyl where the substituents on the phenyl or alkyl are from 1 to 5 of hydroxy, C$_1$–C$_6$ alkoxy, fluoro, R$^1$, R$^2$ independently disubstituted phenyl, R$^1$, R$^2$ independently disubstituted phenyl C$_1$–C$_3$ alkoxy, C$_1$–C$_6$ alkanoyloxy, C$_1$–C$_5$ alkoxycarbonyl, carboxy or formyl where R$^1$, R$^2$, R$^{7a}$, R$^{12a}$, R$^{12b}$, R$^{12c}$, m and v are as defined above;

R$^{16}$ is hydrogen, C$_1$–C$_6$ alkyl or substituted C$_1$–C$_6$ alkyl where the substituents are from 1 to 3 of hydroxy, C$_1$–C$_6$ alkoxy, fluoro, R$^1$, R$^2$ independently disubstituted phenyl, R$^1$, R$^2$ independently disubstituted phenyl $C_1$-$C_3$ alkoxy, $C_1$-$C_5$ alkoxycarbonyl, carboxy or $C_1$-$C_5$ alkanoyl-$C_1$-$C_6$ alkyl where $R^1$ and $R^2$ are as defined above;

$R^6$ is hydrogen, $C_1$-$C_{10}$ alkyl or phenyl $C_1$-$C_{10}$ alkyl;

A is

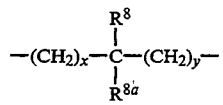

where x and y are independently 0–2;

$R^8$ and $R^{8a}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —S(O)$_m R^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^8$ and $R^{8a}$ can be taken together to form —(CH$_2$)$_t$— where t is 2 to 4; and $R^8$ and $R^{8a}$ can independently be joined to $R^5$ to form alkylene bridges between the terminal nitrogen and the alkyl portion of the A group wherein the bridge contains from one to five carbon atoms;

and pharmaceutically acceptable salts thereof.

3. A compound of claim 2 wherein:

n is 0 or 1;
p is 0 to 2;
q is 0 to 2;
w is 0 or 1;
X is S(O)$_m$ or —CH=CH—;
m is 0 to 1;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m R^{7a}$, $R^{7b}$O(CH$_2$)$_v$—, $R^{7b}$COO(CH$_2$)$_v$—, $R^{7b}$OCO(CH$_2$)$_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl or substituted $C_1$-$C_6$ alkyl where the substituents are phenyl and v is 0 to 2;

$R^{3a}$ and $R^{3b}$ are independently hydrogen, $R^9$, $C_1$-$C_6$ alkyl substituted with $R^9$ or phenoxy substituted with $R^9$;

$R^9$ is

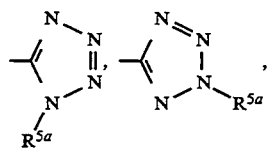

$R^{7b}$O(CH$_2$)$_v$—, $R^{7b}$COO(CH$_2$)$_v$—, $R^{7b}$OCO(CH$_2$)$_v$—, $R^{7b}$CO(CH$_2$)$_v$—, $R^{5b}R^{12b}$N(CH$_2$)$_v$—, $R^{5b}R^{12b}$NCO(CH$_2$)$_v$—, $R^{5b}R^{12c}$NN(R$^{12b}$)CO(CH$_2$)$_v$—, $R^{5b}R^{12b}$NCON(R$^{12a}$)(CH$_2$)$_v$—, $R^{5b}R^{12c}$NN(R$^{12b}$)CSN(R$^{12a}$)(CH$_2$)$_v$—, $R^{5b}R^{12c}$NN(R$^{12b}$)CON(R$^{12a}$)(CH$_2$)$_v$—, $R^{5b}R^{12c}$NN(R$^{12b}$)COO(CH$_2$)$_v$—, $R^{5b}R^{12b}$NCOO(CH$_2$)$_v$— or $R^{13}$OCON(R$^{12a}$)(CH$_2$)$_v$—, where v is 0 to 2;

$R^{12a}$, $R^{12b}$ and $R^{12c}$ are independently $R^{5a}$ or OR$^{5a}$; $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2 and $R^1$ and $R^{10}$ are as defined;

$R^{13}$ is $C_1$-$C_6$ alkyl, substituted $C_1$-$C_6$ alkyl, where the substitutents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^{10}$ and $R^{11}$ are independently hydrogen, $C_1$-$C_6$ alkyl, phenyl $C_1$-$C_6$ alkyl, or $C_1$-$C_5$ alkanoyl-$C_1$-$C_6$ alkyl;

$R^5$, $R^{5a}$ and $R^{5b}$ are independently hydrogen, $C_1$-$C_{10}$ alkyl or substituted $C_1$-$C_{10}$ alkyl where the substituents are from 1 to 5 of hydroxy, $C_1$-$C_6$ alkoxy, fluoro, $R^1$, $R^2$ independently disubstituted phenyl, $C_1$-$C_{20}$ alkanoyloxy, $C_1$-$C_5$ alkoxycarbonyl or carboxy where $R^1$ and $R^2$ are as defined above;

$R^4$ is $R^{14}$ or $C_1$-$C_3$ alkyl substituted with $R^{14}$;

$R^{14}$ is as defined above;

$R^{15a}$ and $R^{15b}$ are independently hydrogen, hydroxy, halogen, —S(O)$_m R^{7a}$, $R^{12a}R^{12c}$N(CH$_2$)$_v$—, $R^{12a}R^{12b}$NCO(CH$_2$)$_v$—, $C_1$-$C_6$ alkoxy, phenyl, substituted phenyl, $C_1$-$C_{10}$ alkyl or substituted $C_1$-$C_{10}$ alkyl where the substitutents on the phenyl or alkyl are from 1 to 5 of hydroxy, $C_1$-$C_6$ alkoxy, $R^1$, $R^2$ independently disubstituted phenyl, $C_1$-$C_6$ alkanoyloxy, $C_1$-$C_5$ alkoxycarbonyl, carboxy or formyl where $R^1$, $R^2$, $R^{7a}$, $R^{12a}$, $R^{12b}$, $R^{12c}$, m and v are as defined above;

$R^{16}$ is hydrogen, $C_1$-$C_6$ alkyl or substituted $C_1$-$C_6$ alkyl where the substitutents are from 1 to 3 of hydroxy, $C_1$-$C_6$ alkoxy, $R^1$, $R^2$ independently disubstituted phenyl, $C_1$-$C_5$ alkoxycarbonyl, carboxy or $C_1$-$C_5$ alkanoyl-$C_1$-$C_6$ alkyl where $R^1$ and $R^2$ are as defined above;

$R^6$ is hydrogen or $C_1$-$C_{10}$ alkyl;

A is

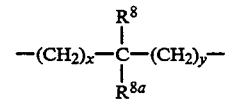

where x and y are independently 0–1;

$R^8$ and $R^{8a}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —S(O)$_m R^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^8$ and $R^{8a}$ can be taken together to form —(CH$_2$)$_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms;

and pharmaceutically acceptable salts thereof.

4. A compound of claim 3 wherein:

n is 0 or 1;
p is 0 to 2;
q is 1;

w is 1;
X is S(O)$_m$ or —CH=CH—;
m is 0 to 1;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$$R^{7a}$, $R^{7b}$O(CH$_2$)$_v$—, $R^{7b}$COO(CH$_2$)$_v$—, phenyl or substituted phenyl where the substituents are from 1 to 3 of halogen, $C_1$-$C_6$ alkyl, $C_1$-$C_6$ alkoxy, or hydroxy;
$R^{7a}$ and $R^{7b}$ are independently hydrogen, $C_1$-$C_6$ alkyl or substituted $C_1$-$C_6$ alkyl where the substituents are phenyl and v is 0 or 1;
$R^{3a}$ and $R^{3b}$ are independently hydrogen, $R^9$ or $C_1$-$C_6$ alkyl substituted with $R^9$;
$R^9$ is

[structure diagram of tetrazole groups with $R^{5a}$ substituents]

$R^{7b}$O(CH$_2$)$_v$—, $R^{7b}$COO(CH$_2$)$_v$—, $R^{7b}$OCO(CH$_2$)$_v$—, $R^{7b}$CO(CH$_2$)$_v$—, $R^{5b}R^{12b}$N(CH$_2$)$_v$—, $R^{5b}R^{12b}$NCO(CH$_2$)$_v$—, $R^{5b}R^{12c}$NN($R^{12b}$)CO(CH$_2$)$_v$—, $R^{5b}R^{12b}$NCON($R^{12a}$)(CH$_2$)$_v$—, $R^{5b}R^{12c}$NN($R^{12b}$)CON($R^{12a}$)(CH$_2$)$_v$—, $R^{5b}R^{12c}$NN($R^{12b}$)COO(CH$_2$)$_v$—, $R^{5b}R^{12b}$NCOO(CH$_2$)$_v$— or $R^{13}$OCON($R^{12a}$)(CH$_2$)$_v$—, where v is 0 to 2;

$R^{12a}$, $R^{12b}$ and $R^{12c}$ are independently $R^{5a}$; $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2 and $R^1$ and $R^{10}$ are as defined;

$R^{13}$ is $C_1$-$C_6$ alkyl, substituted $C_1$-$C_6$ alkyl, where the substitutents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^{10}$ and $R^{11}$ are independently hydrogen, $C_1$-$C_6$ alkyl or $C_1$-$C_5$ alkanoyl-$C_1$-$C_6$ alkyl;

$R^5$, $R^{5a}$ and $R^{5b}$ are independently hydrogen, $C_1$-$C_{10}$ alkyl or substituted $C_1$-$C_{10}$ alkyl where the substitutents are from 1 to 3 of hydroxy, $C_1$-$C_3$ alkoxy, fluoro, $R^1$, $R^2$ independently disubstituted phenyl, $C_1$-$C_{20}$ alkanoyloxy, $C_1$-$C_5$ alkoxycarbonyl or carboxy where $R^1$ and $R^2$ are as defined above;

$R^{15a}$ and $R^{15b}$ are independently hydrogen, hydroxy, halogen, —S(O)$_m$$R^{7a}$, $R^{12a}R^{12c}$N(CH$_2$)$_v$—, $R^{12a}R^{12b}$NCO(CH$_2$)$_v$—, $C_1$-$C_6$ alkoxy, phenyl, substituted phenyl, $C_1$-$C_6$ alkyl or substituted $C_1$-$C_6$ alkyl where the substitutents on the phenyl or alkyl are from 1 to 5 of hydroxy, $C_1$-$C_3$ alkoxy, $R^1$, $R^2$ independently disubstituted phenyl, $C_1$-$C_6$ alkanoyloxy, $C_1$-$C_5$ alkoxycarbonyl, carboxy or formyl where $R^1$, $R^2$, $R^{7a}$, $R^{12a}$, $R^{12b}$, $R^{12c}$, m and v are as defined;

$R^{16}$ is hydrogen, $C_1$-$C_6$ alkyl or substituted $C_1$-$C_6$ alkyl where the substitutents are from 1 to 3 of hydroxy, $C_1$-$C_6$ alkoxy, $R^1$, $R^2$ independently disubstituted phenyl, $C_1$-$C_5$ alkoxycarbonyl, carboxy or $C_1$-$C_5$ alkanoyl-$C_1$-$C_6$ alkyl where $R^1$ and $R^2$ are as defined;

$R^6$ is hydrogen;
A is $$-(CH_2)_x-\underset{\underset{R^{8a}}{|}}{\overset{\overset{R^8}{|}}{C}}-(CH_2)_y-$$

where
x and y are independently 0-1;
$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, S(O)$_m$$R^{7a}$, $C_1$-$C_6$ alkoxy, $C_3$-$C_7$ cycloalkyl, $R^1$, $R^2$ independently disubstituted phenyl, $C_1$-$C_5$ alkanoyloxy, $C_1$-$C_5$ alkoxycarbonyl or carboxy, where $R^1$, $R^2$, $R^{7a}$, and m are as defined; or $R^8$ and $R^{8a}$ can be taken together to form —(CH$_2$)$_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms;
and pharmaceutically acceptable salts thereof.

5. A stereospecific compound of claim 1 having the following structural formula:

[structure diagram of benzazepine compound]

where
$R^1$, $R^2$, X, n, p, q, L, w, $R^{1a}$, $R^{2a}$, $R^{3a}$, $R^4$, $R^5$, $R^6$ and A are as defined in claim 1.

6. A compound of claim 1 which is selected from:
N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;
N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;
N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;
N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;
N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-[(furan-2-yl)methyl]amino-3-methylbutanamide;

N-[1-[[2'-[(Methoxycarbonyl)amino][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

N-[1-[[2'-[(Methylaminocarbonyl)amino][1,1'-biphenyl]-4-yl]-methyl]-7-trifluoromethyl-2,3,4,5-tetrahydro-2-oxo-1H-1-benzazepin-3(R)-yl]-3-[(furan-2-yl)methyl]amino-3-methylbutanamide;

N-[1-[[2'-[(Morpholinocarbonyl)amino][1,1'-biphenyl]-4-yl]methyl]-7-trifluoromethyl-2,3,4,5-tetrahydro-2-oxo-1H-1-benzazepin-3(R)-yl]-3-[(furan-2-yl)methyl]amino-3-methylbutanamide;

N-[1-[[2'-[[(2-Hydroxyethylamino)carbonyl]amino][1,1'-biphenyl]-4-yl]methyl]-7-trifluoromethyl-2,3,4,5-tetrahydro-2-oxo-1H-1-benzazepin-3(R)-yl]-3-[(furan-2-yl)methyl]amino-3-methylbutanamide;

N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-3-[(furan-2-yl)methyl]amino-3-methylbutanamide;

3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;

3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-fluoro-2-oxo-1H-benzazepin-3(R)-yl]butanamide;

3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-methoxy-2-oxo-1H-benzazepin-3(R)-yl]butanamide;

3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-methylthio-2-oxo-1H-benzazepin-3(R)-yl]butanamide;

3-[(Furan-2-yl)methyl]amino-3-methyl-N-[2,3,4,5-tetrahydro-1-[[2'-[[[(methylamino)carbonyl]amino]methyl][1,1'-biphenyl]-4-yl]methyl]-7-trifluoromethyl-2-oxo-1H-benzazepin-3(R)-yl]butanamide;

3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]butanamide;

3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-fluoro-2-oxo-1H-benzazepin-3(R)-yl]butanamide;

3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-methoxy-2-oxo-1H-benzazepin-3(R)-yl]butanamide;

3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-methylthio-2-oxo-1H-benzazepin-3(R)-yl]butanamide;

3-[(Furan-2-yl)methyl]amino-3-methyl-N-[2,3,4,5-tetrahydro-1-[[2'-[[(aminocarbonyl)amino]methyl][1,1'-biphenyl]-4-yl]methyl]-7-trifluoromethyl-2-oxo-1H-benzazepin-3(R)-yl]butanamide;

3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]butanamide;

3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-fluoro-2-oxo-1H-benzazepin-3(R)-yl]butanamide;

3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-methoxy-2-oxo-1H-benzazepin-3(R)-yl]butanamide;

3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-methylthio-2-oxo-1H-benzazepin-3(R)-yl]butanamide;

3-[(Furan-2-yl)methyl]amino-3-methyl-N-[2,3,4,5-tetrahydro-1-[[2'-[[[(ethylamino)carbonyl]amino]methyl][1,1'-biphenyl]-4-yl]methyl]-7-trifluoromethyl-2-oxo-1H-benzazepin-3(R)-yl]butanamide;

3-[(Furan-2-yl)methyl]amino-3-methyl-N-[2,3,4,5-tetrahydro-1-[[2'-[[[(hydroxyethyl)amino]carbonyl]amino]methyl][1,1'-biphenyl]-4-yl]methyl]-2-oxo-1H-benzazepin-3(R)-yl]butanamide;

3-[(Furan-2-yl)methyl]amino-3-methyl-N-[2,3,4,5-tetrahydro-1-[[2'-[[[(hydroxyethyl)amino]carbonyl]amino]methyl][1,1'-biphenyl]-4-yl]methyl]-7-fluoro-2-oxo-1H-benzazepin-3(R)-yl]butanamide;

3-[(Furan-2-yl)methyl]amino-3-methyl-N-[2,3,4,5-tetrahydro-1-[[2'-[[[(hydroxyethyl)amino]carbonyl]amino]methyl][1,1'-biphenyl]-4-yl]methyl]-7-methoxy-2-oxo-1H-benzazepin-3(R)-yl]butanamide;

3-[(Furan-2-yl)methyl]amino-3-methyl-N-[2,3,4,5-tetrahydro-1-[[2'-[[[(hydroxyethyl)amino]carbonyl]amino]methyl][1,1'-biphenyl]-4-yl]methyl]-7-methylthio-2-oxo-1H-benzazepin-3(R)-yl]butanamide;

3-[(Furan-2-yl)methyl]amino-3-methyl-N-[2,3,4,5-tetrahydro-1-[[2'-[[[(hydroxyethyl)amino]carbonyl]amino]methyl][1,1'-biphenyl]-4-yl]methyl]-7-trifluoromethyl-2-oxo-1H-benzazepin-3(R)-yl]butanamide;

3-[(Furan-2-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide;

3-[(Furan-2-yl)methyl]amino-3-methyl-N-[2,3,4,5-tetrahydro-6-fluoro-2-oxo-1-[[2'-(1H-tetrazol-5-yl)[1,1'-biphenyl]-4-yl]methyl]-1H-1-benzazepin-3(R)-yl]butanamide;

3-[(Furan-2-yl)methyl]amino-3-methyl-N-[2,3,4,5-tetrahydro-7-fluoro-2-oxo-1-[[2'-(1H-tetrazol-5-yl)[1,1'-biphenyl]-4-yl]methyl]-1H-1-benzazepin-3(R)-yl]butanamide;

3-[(Furan-2-yl)methyl]amino-3-methyl-N-[2,3,4,5-tetrahydro-7-trifluoromethyl-2-oxo-1-[[2'-(1H-tetrazol-5-yl)[1,1'-biphenyl]-4-yl]methyl]-1H-1-benzazepin-3(R)-yl]butanamide;

3-[(Furan-2-yl)methyl]amino-3-methyl-N-[2,3,4,5-tetrahydro-7-methylthio-2-oxo-1-[[2'-(1H-tetrazol-5-yl)[1,1'-biphenyl]-4-yl]methyl]-1H-1-benzazepin-3(R)-yl]butanamide;

3-[(Furan-2-yl)methyl]amino-3-methyl-N-[2,3,4,5-tetrahydro-7-methoxy-2-oxo-1-[[2'-(1H-tetrazol-5-yl)[1,1'-biphenyl]-4-yl]methyl]-1H-1-benzazepin-3(R)-yl]butanamide;

4'-[[3(R)-[[3-[(Furan-2-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;

4'-[[3(R)-[[3-[(Furan-2-yl)methyl]amino-3-methyl-1-oxobutyl]amino]-7-fluoro-2,3,4,5-tetrahydro-2-oxo-1H-1-benzazepin-1-yl]methyl][1,1'-biphenyl]-2-carboxamide;

4'-[[3(R)-[[3-[(Furan-2-yl)methyl]amino-3-methyl-1-oxobutyl]amino]-7-trifluoromethyl-2,3,4,5-tetrahydro-2-oxo-1H-1-benzazepin-1-yl]methyl][1,1'-biphenyl]-2-carboxamide;

4'-[[3(R)-[[3-[(Furan-2-yl)methyl]amino-3-methyl-1-oxobutyl]amino]-7-methylthio-2,3,4,5-tetrahydro-2-oxo-1H-1-benzazepin-1-yl]methyl][1,1'-biphenyl]-2-carboxamide;

4'-[[3(R)-[[3-[(Furan-2-yl)methyl]amino-3-methyl-1-oxobutyl]amino]-7-methoxy-2,3,4,5-tetrahydro-2-oxo-1H-1-benzazepin-1-yl]methyl][1,1'-biphenyl]-2-carboxamide;

N-Ethyl-4'-[[3(R)-[[3-[(furan-2-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;

N-Ethyl-4'-[[3(R)-[[3-[(furan-2-yl)methyl]amino-3-methyl-1-oxobutyl]amino]-7-fluoro-2,3,4,5-tetrahydro-2-oxo-1H-1-benzazepin-1-yl]methyl][1,1'-biphenyl]-2-carboxamide;

N-Ethyl-4'-[[3(R)-[[3-[(furan-2-yl)methyl]amino-3-methyl-1-oxobutyl]amino]-7-trifluoromethyl-2,3,4,5-tetrahydro-2-oxo-1H-1-benzazepin-1-yl]methyl][1,1'-biphenyl]-2-carboxamide;

N-Ethyl-4'-[[3(R)-[[3-[(furan-2-yl)methyl]amino-3-methyl-1-oxobutyl]amino]-7-methylthio-2,3,4,5-tetrahydro-2-oxo-1H-1-benzazepin-1-yl]methyl][1,1'-biphenyl]-2-carboxamide;

N-Ethyl-4'-[[3(R)-[[3-[(furan-2-yl)methyl]amino-3-methyl-1-oxobutyl]amino]-7-methoxy-2,3,4,5-tetrahydro-2-oxo-1H-1-benzazepin-1-yl]methyl][1,1'-biphenyl]-2-carboxamide;

3-[(Furan-2-yl)methyl]amino-3-methyl-N-[2,3,4,5-tetrahydro-2-oxo-1-[[2'-hydroxymethyl[1,1'-biphenyl]-4-yl]methyl]-1H-1-benzazepin-3(R)-yl]butanamide;

3-[(Furan-2-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

3-[(Furan-2-yl)methyl]amino-3-methyl-N-[8-fluoro-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

3-[(Furan-2-yl)methyl]amino-3-methyl-N-[8-trifluoromethyl-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

3-[(Furan-2-yl)methyl]amino-3-methyl-N-[8-methylthio-2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

4'-[[3(S)-[[3-[(Furan-2-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;

N-ethyl-4'-[[3(S)-[[3-[(Furan-2-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;

N-[5-[[2'-[(Methoxycarbonyl)amino][1,1'-biphenyl]-4-yl]methyl]-2,3,4,5-tetrahydro-4-oxo-1,5-benzothiazepin-3(S)-yl]-3-[(furan-2-yl)methyl]amino-3-methylbutanamide;

N-[5-[[2'-[(Methylaminocarbonyl)amino][1,1'-biphenyl]-4-yl]-methyl]-2,3,4,5-tetrahydro-4-oxo-1,5-benzothiazepin-3(S)-yl]-3-[(furan-2-yl)methyl]amino-3-methylbutanamide;

N-[5-[[2'-[(Morpholinocarbonyl)amino][1,1'-biphenyl]-4-yl]-methyl]-2,3,4,5-tetrahydro-4-oxo-1,5-benzothiazepin-3(S)-yl]-3-[(furan-2-yl)methyl]amino-3-methylbutanamide;

N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[(furan-2-yl)methyl]amino-3-methylbutanamide;

3-[(Furan-2-yl)methyl]amino-3-methyl-N-[2,3,4,5-tetrahydro-5-[[2'-[[(methylamino)carbonyl]amino]methyl][1,1'-biphenyl]-4-yl]methyl]-4-oxo-1,5-benzothiazepin-3(S)-yl]butanamide;

3-[(Furan-2-yl)methyl]amino-3-methyl-N-[2,3,4,5-tetrahydro-5-[[2'-[[(methylamino)carbonyl]amino]methyl][1,1'-biphenyl]-4-yl]methyl]-8-fluoro-4-oxo-1,5-benzothiazepin-3(S)-yl]butanamide;

3-[(Furan-2-yl)methyl]amino-3-methyl-N-[2,3,4,5-tetrahydro-5-[[2'-[[(methylamino)carbonyl]amino]methyl][1,1'-biphenyl]-4-yl]methyl]-8-methoxy-4-oxo-1,5-benzothiazepin-3(S)-yl]butanamide;

3-[(Furan-2-yl)methyl]amino-3-methyl-N-[2,3,4,5-tetrahydro-5-[[2'-[[(methylamino)carbonyl]amino]methyl][1,1'-biphenyl]-4-yl]methyl]-8-methylthio-4-oxo-1,5-benzothiazepin-3(S)-yl]butanamide;

3-[(Furan-2-yl)methyl]amino-3-methyl-N-[2,3,4,5-tetrahydro-5-[[2'-[[(methylamino)carbonyl]amino]methyl][1,1'-biphenyl]-4-yl]methyl]-8-trifluoromethyl-4-oxo-1,5-benzothiazepin-3(S)-yl]butanamide;

3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-4-oxo-1,5-benzothiazepin-3(S)-yl]butanamide;

3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;

3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]butanamide;

3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;

3-[(Furan-2-yl)methyl]amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]butanamide;

3-[(Furan-2-yl)methyl]amino-3-methyl-N-[2,3,4,5-tetrahydro-5-[[2'-[[(ethylamino)carbonyl]amino]methyl][1,1'-biphenyl]-4-yl]methyl]-4-oxo-1,5-benzothiazepin-3(S)-yl]butanamide;

3-[(Furan-2-yl)methyl]amino-3-methyl-N-[2,3,4,5-tetrahydro-5-[[2'-[[(ethylamino)carbonyl]amino]methyl][1,1'-biphenyl]-4-yl]methyl]-8-fluoro-4-oxo-1,5-benzothiazepin-3(S)-yl]butanamide;

3-[(Furan-2-yl)methyl]amino-3-methyl-N-[2,3,4,5-tetrahydro-5-[[2'-[[(ethylamino)carbonyl]amino]methyl][1,1'-biphenyl]-4-yl]methyl]-8-methoxy-4-oxo-1,5-benzothiazepin-3(S)-yl]butanamide;

3-[(Furan-2-yl)methyl]amino-3-methyl-N-[2,3,4,5-tetrahydro-5-[[2'-[[(ethylamino)carbonyl]amino]methyl][1,1'-biphenyl]-4-yl]methyl]-8-methylthio-4-oxo-1,5-benzothiazepin-3(S)-yl]butanamide;

3-[(Furan-2-yl)methyl]amino-3-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzothiazepin-3(S)-yl]butanamide;

3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]butanamide;

3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-fluoro-4-oxo-1,5-benzothiazepin-3(S)-yl]butanamide;

3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-methoxy-4-oxo-1,5-benzothiazepin-3(S)-yl]butanamide;

3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-methylthio-4-oxo-1,5-benzothiazepin-3(S)-yl]butanamide;

3-[(Furan-2-yl)methyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]butanamide;

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[(oxazol-5-yl)methyl]amino-3-methylbutanamide;

N-[1-[[2'-[[(2-Hydroxyethylamino)carbonyl]amino][1,1'-biphenyl]-4-yl]methyl-2,3,4,5-tetrahydro-2-oxo-1H-1-benzazepin-3(R)-yl]-3-[(oxazol-5-yl)methyl]amino-3-methylbutanamide;

3-[(Oxazol-5-yl)methyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;

3-[(Oxazol-5-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide;

N-Ethyl-4'-[[3(R)-[[3-[(oxazol-5-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;

3-[(Oxazol-5-yl)methyl]amino-3-methyl-N-[2,3,4,5-tetrahydro-4-oxo-5-[[2'-(1H-tetrazol-5-yl)[1,1'-biphenyl]-4-yl]methyl]-1,5-benzothiazepin-3(S)-yl]butanamide;

N-Ethyl-4'-[[3(S)-[[3-[(oxazol-5-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;

N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[(oxazol-5-yl)methyl]amino-3-methylbutanamide;

N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[(oxazol-5-yl)methyl]amino-3-methylbutanamide;

3-[(Oxazol-5-yl)methyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[(benzofuran-2-yl)methyl]amino-3-methylbutanamide;

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[(benzofuran-2-yl)methyl]amino-3-methylbutanamide;

3-[(Benzofuran-2-yl)methyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;

3-[(Benzofuran-2-yl)methyl]amino-3-methyl-N-[2,3,4,5-tetrahydro-2-oxo-1-[[2'-(1H-tetrazol-5-yl) [1,1'-biphenyl]-4-yl]methyl]-1H-1-benzazepin-3(R)-yl]butanamide;

N-Ethyl-4'-[[3(R)-[[3-[(benzofuran-2-yl)methyl]amino-3-methyl-1-oxobutyl]amino]-2,3,4,5-tetrahydro-2-oxo-1H-1-benzazepin-1-yl]methyl][1,1'-biphenyl]-2-carboxamide;

3-[(Benzofuran-2-yl)methyl]amino-3-methyl-N-[2,3,4,5-tetrahydro-4-oxo-5-[[2'-(1H-tetrazol-5-yl) [1,1'-biphenyl]-4-yl]methyl]-1,5-benzothiazepin-3(S)-yl]butanamide;

N-Ethyl-4'-[[3(S)-[[3-[(benzofuran-2-yl)methyl]amino-3-methyl-1-oxobutyl]amino]-2,3,4,5-tetrahydro-4-oxo-1,5-benzothiazepin-5(2H)-yl]methyl][1,1'-biphenyl]-2-carboxamide;

N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[(benzofuran-2-yl)methyl]amino-3-methylbutanamide;

N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[(benzofuran-2-yl)methyl]amino-3-methylbutanamide; and 3-[(Benzofuran-2-yl)methyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide.

* * * * *